US012716097B2

(12) United States Patent
June

(10) Patent No.: US 12,716,097 B2
(45) Date of Patent: Aug. 25, 2026

(54) BIOMARKERS FOR THE DIAGNOSIS OF ATRIAL FIBRILLATION CAUSE OF STROKE

(71) Applicant: Ischemia Care LLC, Oxford, OH (US)

(72) Inventor: Jeffrey Gerard June, Oxford, OH (US)

(73) Assignee: Ischemia Care LLC, Oxford, OH (US)

( * ) Notice: Subject to any disclaimer, the term of this patent is extended or adjusted under 35 U.S.C. 154(b) by 948 days.

(21) Appl. No.: 17/782,831

(22) PCT Filed: Nov. 23, 2020

(86) PCT No.: PCT/US2020/061761
§ 371 (c)(1),
(2) Date: Jun. 6, 2022

(87) PCT Pub. No.: WO2021/118796
PCT Pub. Date: Jun. 17, 2021

(65) Prior Publication Data

US 2023/0002829 A1 Jan. 5, 2023

Related U.S. Application Data

(60) Provisional application No. 62/948,170, filed on Dec. 13, 2019.

(51) Int. Cl.

| | |
|---|---|
| ***C12Q 1/68*** | (2018.01) |
| ***C12P 19/34*** | (2006.01) |
| ***C12Q 1/6883*** | (2018.01) |
| ***G01N 33/68*** | (2006.01) |

(52) U.S. Cl.
CPC ....... *C12Q 1/6883* (2013.01); *G01N 33/6893* (2013.01); *C12Q 2600/158* (2013.01); *G01N 2333/912* (2013.01); *G01N 2800/326* (2013.01)

(58) Field of Classification Search
CPC .................................................... C12Q 1/6883
See application file for complete search history.

(56) References Cited

U.S. PATENT DOCUMENTS

2011/0009861 A1 1/2011 Mukherjee et al.
2012/0021989 A1 1/2012 Holm et al.
2012/0065075 A1 3/2012 Hamet et al.
2016/0265059 A1 9/2016 Sharp et al.
2019/0162737 A1 5/2019 Karl et al.

OTHER PUBLICATIONS

Huichun Xu, et al. "Gene Expression in Peripheral Blood Differs after Cardioembolic Compared with Large-Vessel Atherosclerotic Stroke: Biomarkers for the Etiology of Ischemic Stroke" Journal of Cerebral Blood Flow & Metabolism, vol. 28, Issue 7, Jul. 2008, pp. 1320-1328 (Year: 2008).*

Jauch, E, Barreto, A, Broderick, J, Char, D, Cucchiara, B, Hicks, W, Huang, D. (2018). Abstract 67: RNA Expression Differentiates Large Artery and Cardioembolic Stroke: A Pilot Analysis From the BASE Trial. Stroke, 49 (Suppl_1), A67. (Jan. 2018 Conference) (Year: 2018).*

Sasha Vaziri, et al. Predictive performance of the American College of Surgeons universal risk calculator in neurosurgical patients. J Neurosurg 128:942-947, 2018 (Year: 2018).*

Hoshikawa, Y. et al. "Hypoxia induces different genes in the lungs of rats compared with mice" Physiol Genomics 12: 209-219, 2003 (Year: 2003).*

Vivian G. Cheung. "Natural variation in human gene expression assessed in lymphoblastoid cells" Nature Genetics, vol. 33, Mar. 2003, pp. 422-425. (Year: 2003).*

J. Perren Cobb, et al. "Sepsis gene expression profiling: Murine splenic compared with hepatic responses determined by using complementary DNA microarrays" Crit Care Med 2002 vol. 30, No. 12, pp. 2711-2721 (Year: 2002).*

Guoan Chen, et al. "Discordant Protein and mRNA Expression in Lung Adenocarcinomas" Molecular & Cellular Proteomics 1.4, pp. 304-313 (Year: 2002).*

* cited by examiner

*Primary Examiner* — Stephen T Kapushoc
(74) *Attorney, Agent, or Firm* — Jenei LLC

(57) ABSTRACT

This invention provides gene expression profiles useful for diagnosing atrial fibrillation in ischemic stroke and for distinguishing atrial fibrillation in ischemic stroke from arterial (large vessel) stroke or embolic stroke of undetermined source (ESUS). In another aspect, the present invention is the provision of an improved method for prognosis of an outcome or assessing the risk of a patient having suffered a stroke or a transient ischemic attack, comprising determining the level of expression of at least one biomarker in a sample of the patient.

13 Claims, No Drawings

BIOMARKERS FOR THE DIAGNOSIS OF ATRIAL FIBRILLATION CAUSE OF STROKE

CROSS-REFERENCE TO RELATED APPLICATIONS

This application claims the benefit of priority under 35 U.S.C. § 119(e) to U.S. Provisional Application Ser. No. 62/948,170, entitled "BIOMARKERS FOR THE DIAGNOSIS OF ATRIAL FIBRILLATION CAUSE OF STROKE", filed Dec. 13, 2019, the contents of which are hereby incorporated by reference in their entirety for any purpose.

BACKGROUND

1. Technical Field

The present invention relates to gene expression profiling to differentiate ischemic stroke, transient ischemic attack, and patients that present with stroke like symptoms caused by atrial fibrillation.

2. Description of the Related Art

Atrial fibrillation (AF) is an abnormal heart rhythm (cardiac arrhythmia) which involves the two small, upper heart chambers (the atria). Heart beats in a normal heart begin after electricity generated in the atria by the sinoatrial node spreads through the heart and causes contraction of the heart muscle and pumping of blood. In AF, the regular electrical impulses of the sinoatrial node are replaced by disorganized, rapid electrical impulses which result in irregular heartbeat.

Atrial fibrillation is the most common cardiac arrhythmia. The risk of developing atrial fibrillation increases with age. That is, AF affects four percent of individuals in their 80s. An individual may spontaneously alternate between AF and a normal rhythm (paroxysmal atrial fibrillation) or may continue with AF as the dominant cardiac rhythm without reversion to the normal rhythm (chronic atrial fibrillation). Atrial fibrillation is often asymptomatic, but may result in symptoms of palpitations, fainting, chest pain, or even heart failure. These symptoms are especially common when atrial fibrillation results in a heart rate, which is either too fast or too slow. In addition, the erratic motion of the atria leads to blood stagnation (stasis) which increases the risk of blood clots that may travel from the heart to the brain and other areas. Thus, AF is an important risk factor for stroke, the most feared complication of atrial fibrillation.

The symptoms of atrial fibrillation may be treated with medications which slow the heart rate. Several medications as well as electrical cardioversion may be used to convert AF to a normal heart rhythm. Surgical and catheter-based therapies may also be used to prevent atrial fibrillation in certain individuals. People with AF are often given blood thinners such as warfarin to protect them from strokes.

Treatment of atrial fibrillation is directed by two main objectives: (i) prevent temporary circulatory instability; (ii) prevent stroke. The most common methods for achieving the former includes rate and rhythm control, while anticoagulation is usually the desired method for the latter (Prystowsky E. N., Am J Cardiol; 85, 3D-11D (2000); van Walraven C, et al., Jama. 288, 2441-2448 (2002)). Common methods for rate control, i.e. for reducing heart rate to normal, include beta blockers (e.g., metotprolol), cardiac glycosides (e.g., digoxin) and calcium channel blockers (e.g., verapamil). All these medications work by slowing down the generation of pulses from the atria, and the conduction from the atria to the ventricles. Other drugs commonly used include quinidine, flecamide, propafenone, disopyramide, sotalol and amiodarone. Rhythm control can be achieved by electrical cardioversion, i.e. by applying DC electrical shock, or by chemical cardioversion, using drugs such as amiodarione, propafenone and flecamide.

Preventive measures for stroke include anticoagulants, novel oral anticoagulants (NOAC) or direct oral anticoagulants (DOAC). Representative examples of anticoagulant agents are Dalteparin (e.g., Fragmin), Danaparoid (e.g., Orgaran), Enoxaparin (e.g., Lovenox), Heparin (various), Tinzaparin (e.g., Innohep), Warfarin (e.g., Coumadin). DOACs are oral medications that specifically inhibit factors IIa or Xa. They are also known as new oral anticoagulants NOACs or target-specific oral anticoagulants (TSOACs). Some patients with lone atrial fibrillation are sometimes treated with aspirin or clopidogrel. There is evidence that aspirin and clopidogrel are effective when used together, but the combination is still inferior to warfarin (Connolly S., et al. Lancet; 367, 1903-1912 (2006)). (2) The new anticoagulant ximelagatran has been shown to prevent stroke with equal efficacy as warfarin, without the difficult monitoring process associated with warfarin and with possibly fewer adverse hemorrhagic events.

Stroke is a common and serious disease. Each year in the United States more than 600,000 individuals suffer a stroke and more than 160,000 die from stroke-related causes (Sacco, R. L. et al., Stroke 28, 1507-17 (1997)). Furthermore, over 300,000 individuals present with Transient Ischemic Attack, a mild form of stroke, every year in the US. In western countries stroke is the leading cause of severe disability and the third leading cause of death (Bonita, R, Lancet 339, 342-4 (1992)). The lifetime risk of those who reach the age of 40 exceeds 10%.

The clinical phenotype of stroke is complex but is broadly divided into ischemic (accounting for 80-90%) and hemorrhagic stroke (10-20%) (Caplan, L. R Caplan's Stroke: A Clinical Approach, 1-556 (Butterworth-Heinemann, 2000)). Ischemic stroke is further subdivided into large vessel occlusive disease (referred to here as carotid stroke), usually due to atherosclerotic involvement of the common and internal carotid arteries, small vessel occlusive disease, thought to be a non-atherosclerotic narrowing of small end-arteries within the brain, strokes of unknown causes (commonly referred to as cryptogenic or embolic strokes of unknown source (ESUS)), strokes of other known causes, and cardiogenic stroke due to blood clots arising from the heart usually on the background of atrial fibrillation or ischemic (atherosclerotic) heart disease (Adams, H. P., Jr. et al., Stroke 24, 35-41 (1993)).

AF is an independent risk factor for stroke, increasing risk about 5-fold. The risk for stroke attributable to AF increases with age. AF is responsible for about 15-20% of all strokes. AF is also an independent risk factor for stroke recurrence and stroke severity. A recent report showed people who had AF and were not treated with anticoagulants had a 2.1-fold increase in risk for recurrent stroke and a 2.4 fold increase in risk for recurrent severe stroke. People who have stroke caused by AF have been reported as 2.23 times more likely to be bedridden compared to those who have strokes from other causes.

The present invention is based, in part, on using gene expression profiling to distinguish patients who have suffered or are at risk of suffering atrial fibrillation in ischemic stroke from patients who have suffered or are at risk of suffering arterial (large vessel) stroke using a gene expression profiling. The gene expression profiles can be used to categorize, diagnose and treat stroke patients by cause based on a profile of differentially expressed genes. The present invention is based, in part, on the identification of a profile of differentially expressed genes useful to distinguish atrial fibrillation in ischemic stroke from arterial (large vessel) stroke and to predict etiology of stroke of unclear cause.

BRIEF SUMMARY

In one aspect, the present disclosure provides biomarkers useful for differentiating stroke patients with atrial fibrillation from those with large artery stroke.

In another aspect, the present invention is the provision of an improved method for prognosis of an outcome or assessing the risk of a patient having suffered a stroke or a transient ischemic attack, comprising determining the level of expression of at least one biomarker in a sample of the patient.

The present invention provides for methods of using gene expression profiling to distinguish patients who have suffered or are at risk of suffering atrial fibrillation in ischemic stroke from patients who have suffered or are at risk of suffering arterial (large vessel) stroke or embolic stroke of undetermined source (ESUS), a type of ischemic stroke with an unknown origin, defined as a non-lacunar brain infarct without proximal arterial stenosis or cardioembolic sources.

Accordingly, in one aspect, the invention provides methods for diagnosing the occurrence of atrial fibrillation in ischemic stroke or a predisposition for experiencing atrial fibrillation in ischemic stroke. In some embodiments, the methods comprise:

determining a level of expression of a plurality of atrial fibrillation in ischemic stroke-associated biomarkers in a biological sample from a patient, wherein the biomarkers are selected from ELL2, GLIPR1, and MAPKAPK3 genes; and comparing the level of expression of the atrial fibrillation in ischemic stroke-associated biomarkers to the expression level of a plurality of stably expressed endogenous reference biomarkers;

wherein an increase of the expression level of one or more biomarkers selected from the group consisting of ELL2, GLIPR1, and MAPKAPK3 genes compared to the expression level of the plurality of endogenous reference biomarkers is correlative with or indicates that the patient suffers from or is at risk of experiencing atrial fibrillation in ischemic stroke, thereby diagnosing the occurrence of atrial fibrillation in ischemic stroke or the predisposition for experiencing atrial fibrillation in ischemic stroke.

In a related aspect, the invention provides methods for distinguishing the occurrence of atrial fibrillation in ischemic stroke or a predisposition for experiencing atrial fibrillation in ischemic stroke from the occurrence of arterial (large vessel) stroke or embolic stroke of undetermined source (ESUS) or a predisposition for experiencing arterial (large vessel) stroke or embolic stroke of undetermined source (ESUS).

In some embodiments, the methods comprise:

determining a level of expression of a plurality of atrial fibrillation in ischemic stroke-associated biomarkers in a biological sample from a patient, wherein the biomarkers are ELL2, GLIPR1, and MAPKAPK3; and comparing the level of expression of the atrial fibrillation in ischemic stroke-associated biomarkers to the expression level of a plurality of stably expressed endogenous reference biomarkers;

wherein an increase of the expression level of one or more biomarkers selected from the group consisting of ELL2, GLIPR1, and MAPKAPK3 compared to the expression level of the plurality of endogenous reference biomarkers is correlative with or indicates that the patient suffers from or is at risk of experiencing atrial fibrillation in ischemic stroke; and/or wherein a decrease of the expression level of one or more biomarkers selected from the group consisting of ELL2, GLIPR1, and MAPKAPK3 compared to the expression level of the plurality of endogenous reference biomarkers is correlative with or indicates that the patient suffers from or is at risk of experiencing arterial (large vessel) stroke or embolic stroke of undetermined source (ESUS);

thereby distinguishing the occurrence of atrial fibrillation in ischemic stroke or the predisposition for experiencing atrial fibrillation in ischemic stroke from the occurrence of arterial (large vessel) stroke or embolic stroke of undetermined source (ESUS) or a predisposition for experiencing arterial (large vessel) stroke or embolic stroke of undetermined source (ESUS).

In a related aspect, the invention provides methods for diagnosing atrial fibrillation in ischemic stroke or a predisposition for developing atrial fibrillation in ischemic stroke. In some embodiments, the methods comprise:

determining a level of expression of a plurality of atrial fibrillation in ischemic stroke-associated biomarkers in a biological sample from a patient, wherein an increase or decrease of the level compared to a control level is correlative with or indicates that the patient suffers from or is at risk of developing atrial fibrillation in ischemic stroke;

wherein an increase of the expression level of one or more biomarkers selected from the group consisting of ELL2, GLIPR1, and MAPKAPK3, compared to the control level is correlative with or indicates that the patient suffers from or is at risk of experiencing atrial fibrillation in ischemic stroke, thereby diagnosing the occurrence of atrial fibrillation in ischemic stroke or the predisposition for experiencing atrial fibrillation in ischemic stroke.

In some embodiments, the control is the expression level of one or more stably expressed endogenous reference biomarkers.

With respect to the embodiments, in some embodiments, an increase of the expression level of one or more biomarkers selected from the group consisting of ELL2, GLIPR1, and MAPKAPK3, and/or a decrease of the expression level of one or more biomarkers selected from the group consisting of ELL2, GLIPR1, and MAPKAPK3, compared to the expression level of the plurality of endogenous reference biomarkers is correlative with or indicates that the patient suffers from or is at risk of experiencing atrial fibrillation in ischemic stroke.

In some embodiments, a decrease of the expression level of one or more biomarkers selected from the group consisting of ELL2, GLIPR1, and MAPKAPK3, compared to the expression level of the plurality of endogenous reference biomarkers is correlative with or indicates that the patient suffers from or is at risk of experiencing arterial (large vessel) stroke or embolic stroke of undetermined source (ESUS).

In some embodiments, an increase of the expression level of one or more biomarkers selected from the group consisting of ELL2, GLIPR1, and MAPKAPK3, compared to the expression level of the plurality of endogenous reference biomarkers is correlative with or indicates that the patient suffers from or is at risk of experiencing atrial fibrillation in ischemic stroke.

In some embodiments, a decrease of the expression level of one or more biomarkers selected from the group consisting of ELL2, GLIPR1, and MAPKAPK3, compared to the expression level of the plurality of endogenous reference biomarkers is correlative with or indicates that the patient suffers from or is at risk of experiencing arterial (large vessel) stroke or embolic stroke of undetermined source (ESUS).

In some embodiments, an increase of the expression level of one or more biomarkers selected from the group consisting of ELL2, GLIPR1, and MAPKAPK3 and/or a decrease of the expression level of one or more biomarkers selected from the group consisting of ELL2, GLIPR1, and MAPKAPK3, compared to the expression level of the plurality of endogenous reference biomarkers is correlative with or indicates that the patient suffers from or is at risk of experiencing atrial fibrillation in ischemic stroke.

In various embodiments, the expression levels of the biomarkers are concurrently or sequentially determined.

The biomarkers described herein for the diagnosis of the occurrence and risk of stroke can be used together, e.g., on a single microarray or in a single assay procedure. The biomarkers also find use independently for the diagnosis of the occurrence of stroke, e.g., in conjunction with alternative methods for determining the cause of stroke, and for determining the cause of stroke, e.g., in conjunction with alternative methods for determining whether a stroke has occurred.

In some embodiments, the methods further comprise the step of obtaining a biological sample from the patient. In some embodiments, the biological sample is blood, serum or plasma.

In some embodiments, the method is performed in a clinical laboratory. In some embodiments, the method is performed at the point of care.

In some embodiments, the plurality of stably expressed endogenous reference biomarkers are selected from USP7, MAPRE2, CSNK1G2, SAFB2, PRKAR2A, PI4 KB, CRTC1, HADHA, MAP1LC3B, KATS, GTSE1, CDC2L1///CDC2L2, TCF25, CHP, LRRC40, hCG 2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHCS, C9orf23, LRRC45, NACC1, LOC100133445///LOC115110 and PEX16.

In some embodiments, the atrial fibrillation in ischemic stroke-associated biomarkers are overexpressed or underexpressed at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, or more, in comparison to the expression levels of a plurality of stably expressed endogenous reference biomarkers.

In some embodiments, the expression levels of 2, 3, 4, 5, 6, 7, 8, 9, 10, 15, 20, 25, 30, 35, or all the endogenous reference biomarkers selected from the group consisting of USP7, MAPRE2, CSNK1G2, SAFB2, PRKAR2A, PI4 KB, CRTC1, HADHA, MAP1LC3B, KATS, CDC2L1///CDC2L2, GTSE1, CDC2L1///CDC2L2, TCF25, CHP, LRRC40, hCG 2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHCS, C9orf23, LRRC45, NACC1, LOC100133445///LOC115110, PEX16 are determined as a control.

In some embodiments, the level of expression of 1, 2 or 3 of the atrial fibrillation in ischemic stroke-associated biomarkers are determined.

In some embodiments, the determining step is performed within 72 hours, for example, within 60 hours, 48 hours, 36 hours, 24 hours, 12 hours, 6 hours or 3 hours, after a suspected ischemic event.

In some embodiments, the patient is asymptomatic. In some cases, the subject is asymptomatic, but may have a risk or predisposition to experiencing ischemic stroke, e.g., based on genetics, a related disease condition, environment, or lifestyle. In some embodiments, the patient has one or more vascular risk factors, e.g., hypertension, diabetes mellitus, hyperlipidemia, or tobacco smoking.

In some embodiments, the patient is exhibiting symptoms of ischemic stroke, e.g., of having experienced an ischemic event, of experiencing an ischemic event, or of an imminent ischemic event. In some embodiments, the patient has suffered an ischemic event. In some embodiments, the determining step is performed at 3 or fewer hours after the ischemic event. In some embodiments, the determining step is performed 3 or more hours after the ischemic event.

In some embodiments, the patient has at least one vascular risk factor. In some embodiments, the patient has experienced a small deep infarction (SDI). In some embodiments, the patient shows evidence of microhemorrhage. In some embodiments, the patient is non-Caucasian. In some embodiments, the patient does not have arterial disease ipsilateral to the stroke.

In various embodiments, the methods, particularly performance of the comparison step, are computer implemented. Such computer-implemented methods may also provide an output of the comparison of expression levels.

Methods for determining the occurrence or predisposition of an atrial fibrillation in ischemic stroke may further comprise the step of determining whether the patient has suffered a myocardial infarction or whether the patient has vascular risk factors. Methods for determining the occurrence or predisposition of an atrial fibrillation in ischemic stroke may further comprise the step of determining whether the patient has evidence of microhemorrhage or whether the patient has arterial disease or whether the patient has cerebral vascular disease. Methods for determining the occurrence or predisposition of an atrial fibrillation in ischemic stroke may further comprise the step of determining whether the patient has suffered a small deep infarction (SDI).

In some embodiments, the level of expression of the biomarker is determined at the transcriptional level. In some embodiments, the level of expression is determined by detecting hybridization of an atrial fibrillation in ischemic stroke-associated gene probe to gene transcripts of the biomarkers in the biological sample.

In some embodiments, the methods further comprise the step of performing additional diagnostic tests useful for identifying whether a patient has experienced or has a predisposition to experience atrial fibrillation in ischemic stroke, e.g., based on imaging or ultrasound techniques. In various embodiments, the methods further comprise performing one or more diagnostic tests selected from the group consisting of X-ray computed tomography (CT), magnetic resonance imaging (MRI) brain scanning, vascular imaging of the head and neck with doppler or magnetic resonance angiography (MRA), CT angiography (CTA), electrocardiogram (e.g., EKG or ECG), cardiac ultrasound and cardiac monitoring. In various embodiments, the patient is subjected to cardiac monitoring for at least 2 days, e.g., for 2-30 days or for 7-21 days, e.g., for 2, 5, 7, 10, 12, 14, 18, 20, 21, 25, 28, 30, or more days, as appropriate. In various embodiments, the location of the infarction is determined. An infarction located in a subcortical region of the brain is associated with or correlated with a diagnosis of atrial fibrillation in ischemic stroke. An infarction located in a cortical region of the brain, e.g., in regions of the penetrating arteries, e.g., basal ganglia, thalamus, internal capsule, corona radiata and/or pons, is associated with or correlated with a diagnosis of non-atrial fibrillation in ischemic stroke. In some embodiments, the size of the infarction is determined.

In some embodiments, the methods further comprise the step of recommending or providing a regime of treatment to the patient appropriate to the determined cause of stroke. For example, in patients diagnosed as experiencing or having a predisposition for experiencing atrial fibrillation in ischemic stroke, the methods further provide for recommending or providing a regime of treatment or prevention for atrial fibrillation in ischemic stroke.

In some forms, a subject likely to have a recurrence of atrial fibrillation following a cardioversion procedure can indicate that the subject should be treated with an implantable pacer. In some forms, a subject likely to have a recurrence of atrial fibrillation following a cardioversion procedure can indicate that the subject should be treated treatment with pharmacological rate control. In some forms, a subject likely to have a recurrence of atrial fibrillation following a cardioversion procedure can indicate that the subject should be treated treatment with ablation. In some forms, a subject not likely to have a recurrence of atrial fibrillation following a cardioversion procedure can indicate that the subject should be treated treatment with cardioversion.

In various embodiments, the methods may further comprise the step of determining the cause or risk of ischemic stroke if the patient has experienced or has a predisposition to experience arterial (large vessel) stroke or embolic stroke of undetermined source (ESUS). The methods may further comprise the step of recommending or providing a regime of treatment to the patient appropriate to the determined cause of arterial (large vessel) stroke or embolic stroke of undetermined source (ESUS). For example, in patients diagnosed as experiencing or having a predisposition for experiencing cardioembolic stroke, the methods further provide for recommending or providing a regime of treatment or prevention for cardioembolic stroke. In patients diagnosed as experiencing or having a predisposition for experiencing carotid stenosis, the methods further provide for recommending or providing a regime of treatment or prevention for carotid stenosis. In patients diagnosed as experiencing or having a predisposition for experiencing atrial fibrillation, the methods further provide for recommending or providing a regime of treatment or prevention for atrial fibrillation. In patients diagnosed as experiencing or having a predisposition for experiencing transient ischemic attack, the methods further provide for recommending or providing a regime of treatment or prevention for transient ischemic attack.

With respect to embodiments for determination of the level of expression of the biomarkers, in some embodiments, the level of expression of the biomarker is determined at the transcriptional level. For example, in some embodiments, the level of expression is determined by detecting hybridization of an ischemic stroke-associated gene probe to gene transcripts of the biomarkers in the biological sample. In some embodiments, the hybridization step is performed on a nucleic acid array chip. In some embodiments, the hybridization step is performed in a microfluidics assay plate. In some embodiments, the level of expression is determined by amplification of gene transcripts of the biomarkers. In some embodiments, the amplification reaction is a polymerase chain reaction (PCR). In some embodiments, the level of expression of the biomarker is determined at the protein level.

Quantitative PCR (or qPCR), microarrays and RNA sequencing are all usable assays for gene expression analysis in the present invention. One method of choice for nucleic acid (DNA, RNA) quantification is real-time PCR or quantitative PCR (qPCR). The method's name derives from the fact that the amplification of DNA by polymerase chain reaction (PCR) is monitored in real time. It is a quantitative method in contrast to conventional PCR, meaning that it enables the determination of exact amounts (relative or absolute) of amplified DNA in samples. Conversely, amplified DNA can only be detected after the amplification had been carried out (end-point detection) in conventional PCR.

Furthermore, the present invention also relates to a kit for prognosis of an outcome or assessing the risk of a patient having suffered a stroke or a transient ischemic attack, the kit comprising one or more capture probes (preferably antibodies or functional fragments thereof) directed against marker peptides or fragments thereof or precursors or fragments thereof selected from the group comprising ELL2, GLIPR1, and MAPKAPK3. The kit may additionally comprise reagents necessary for detection, such as buffers. In addition, the kit may also comprise one or more standard samples, i.e. one or more samples of defined concentration of one or more of the marker peptides.

In a further aspect, the invention provides a solid support comprising a plurality of nucleic acids that hybridize to a plurality of atrial fibrillation in ischemic stroke-associated genes selected from the group consisting of ELL2, GLIPR1, and MAPKAPK3. As appropriate, the solid support may comprise, 2, 3, 4, 5, 10, 15, 20, 25, 30, 35, 40 or more, nucleic acids that hybridize to a plurality of atrial fibrillation in ischemic stroke-associated genes. The solid support may be provided in a kit.

In various embodiments, the solid support further comprises a plurality of nucleic acids that hybridize to a plurality of endogenous reference genes selected from the group consisting of USP7, MAPRE2, CSNK1G2, SAFB2, PRKAR2A, PI4 KB, CRTC1, HADHA, MAP1LC3B, KATS, CDC2L1///CDC2L2, GTSE1, TCF25, CHP, LRRC40, hCG 2003956///LYPLA2///LYPLA2P 1, DAXX, UBE2NL, EIF1, KCMF1, PRKRIP1, CHMP4A, TMEM184C, TINF2, PODNL1, FBXO42, LOC441258, RRP1, C10orf104, ZDHHCS, C9orf23, LRRC45, NACC1, LOC100133445///LOC115110, PEX16.

In some embodiments, the solid support is a microarray. In various embodiments, the microarray has 100, 50, 25, 10 or fewer hybridizing nucleic acids. In various embodiments, the microarray does not comprise nucleic acids that hybridize to genes whose expression is not correlative of or associated with ischemia.

DETAILED DESCRIPTION

According to aspects of the present disclosure, the present invention provides biomarkers useful for differentiating stroke patients with atrial fibrillation from those with large artery stroke. The present invention provides for methods of using gene expression profiling to distinguish patients who have suffered or are at risk of suffering atrial fibrillation in ischemic stroke from patients who have suffered or are at risk of suffering arterial (large vessel) stroke or embolic stroke of undetermined source (ESUS), a type of ischemic stroke with an unknown origin, defined as a non-lacunar brain infarct without proximal arterial stenosis or cardioembolic sources.

In the following detailed description of exemplary embodiments of the disclosure, specific exemplary embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well-known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 3rd ed. (2001) Cold Spring Harbor Laboratory Press, Cold Spring Harbor, N.Y. and Ausubel, et al., CURRENT PROTOCOLS IN MOLECULAR BIOLOGY, 1990-2008, Wiley Interscience), which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

The expression or term "atrial fibrillation" or "AF" as used herein refers to atrial fibrillation (AF) as commonly defined according to established medical criteria. Generally, AF is characterized by an abnormal heart rhythm (cardiac arrhythmia) which involves the two small, upper heart chambers (the atria). Heart beat in a normal heart starts after electricity generated in the atria by the sinoatrial node spreads through the heart and causes contraction of the heart muscle and pumping of the blood. In AF, the regular electrical impulses of the sinoatrial node are replaced by disorganized, rapid electrical impulses which result in irregular heartbeat. There is a lack of unity in the function of the contracting cells of the heart muscle. AF is often asymptomatic but may result in symptoms of palpitations, exercise intolerance, fainting, shortness of breadth, chest pain or even heart failure. The erratic motion of the atria leads to blood stagnation (stasis) which increases the risk of blood clots that may travel from the heart to the brain and cause a stroke.

The term "atrial fibrillation therapeutic agent" refers to an agent that can be used to ameliorate or prevent symptoms associated with atrial fibrillation. Similarly, the term "stroke therapeutic agent" refers to an agent that can be used to ameliorate or prevent symptoms associated with stroke, including ischemic stroke.

The term "atrial fibrillation-associated nucleic acid", as described herein, refers to a nucleic acid that has been found to be associated to atrial fibrillation and/or stroke. This includes, but is not limited to, the markers and haplotypes described herein.

The term "antisense agent" or "antisense oligonucleotide" refers, as described herein, to molecules, or compositions comprising molecules, which include a sequence of purine a pyrimidine heterocyclic bases, supported by a backbone, which are effective to hydrogen bond to a corresponding contiguous bases in a target nucleic acid sequence. The backbone is composed of subunit backbone moieties supporting the purine a pyrimidine heterocyclic bases at positions which allow such hydrogen bonding. These backbone moieties are cyclic moieties of 5 to 7 atoms in size, linked together by phosphorous-containing linkage units of one to three atoms in length. In certain preferred embodiments, the antisense agent comprises an oligonucleotide molecule.

"Ischemia" or "ischemic event" as used herein refers to diseases and disorders characterized by inadequate blood supply (i.e., circulation) to a local area due to blockage of the blood vessels to the area. Ischemia includes for example, strokes and transient ischemic attacks. Strokes include, e.g., ischemic stroke (including, but not limited to, cardioembolic strokes, atheroembolic or atherothrombotic strokes, i.e., strokes caused by atherosclerosis in the carotid, aorta, heart, and brain, small vessel strokes (i.e., atrial fibrillation in ischemic strokes), strokes caused by diseases of the vessel wall, i.e., vasculitis, strokes caused by infection, strokes caused by hematological disorders, strokes caused by migraines, and strokes caused by medications such as hormone therapy), hemorrhagic ischemic stroke, intracerebral hemorrhage, and subarachnoid hemorrhage.

The term "small deep infarct" or "small deep infarction" or "SDI" interchangeably refer to focal infarction of the brain due to an uncertain cause, including but not limited to, cardioembolic, atheroembolic, atherosclerotic disease of the parent artery or disease of the perforating artery.

The term "lacunar stroke" or "lacune" interchangeably refer to focal infarction of the brain due to perforating branch occlusion from microatheroma or lipohyalinosis. Implicit in this definition of atrial fibrillation in ischemic stroke is that the: 1) infarction is not due to cardioembolic source; 2) infarction is not due to atherosclerotic disease of parent arteries; 3) infarction occurs in regions of the brain supplied by penetrating arteries, e.g., basal ganglia, thalamus, internal capsule, corona radiata or pons; 4) atrial fibrillation in ischemic stroke is oftentimes associated with the presence of hypertension, diabetes or other vascular risk factors; and 5) infarcts tend to be smaller, generally less than 50 mm in diameter. When the cause of stroke is uncertain or likely other than perforating artery disease, then the more general term—small deep infarct—is appropriate. See, e.g., Caplan, Stroke (2003) 34(3):653-9; Norrving, Pract Neurol (2008) 8:222-228; Lastilla, Clin Exp Hypertens. (2006) 28(3-4):205-15; and Arboix and Marti Vilalta, Expert Rev Neurother. (2009) 9(2):179-96.

The term "transient ischemic attack," "TIA," or "mini-stroke" interchangeably refer to a change in the blood supply to a particular area of the brain, resulting in brief neurologic dysfunction that persists, by definition, for less than 24 hours. By definition, a TIA resolves within 24 hours, but most TIA symptoms resolve within 1 hour. If symptoms persist longer, then it is categorized as a stroke. Symptoms include temporary loss of vision (typically amaurosis fugax); difficulty speaking (aphasia); weakness on one side of the body (hemiparesis); numbness or tingling (paresthesia), usually on one side of the body, and dizziness, lack of coordination or poor balance. The symptoms of a TIA usually last a few minutes and with resolution of most symptoms within 60 minutes. TIAs are "warning strokes" that produce stroke-like symptoms but no lasting damage. Recognizing and treating TIAs can reduce the risk of a major stroke.

The term "outcome" herein relates for instance to the survival of the patient after a defined time, e.g., after 5 days, 4 weeks, 3 months, 1 year or re-stroke or to a functional outcome. Most preferably the outcome 3 months after the stroke or TIA is predicted. The term "functional outcome" in the context of the present invention relates to the degree of severity of the disease, i.e. the state of health the patient after a defined time, e.g after 5 days, 4 weeks, 3 months, or 1 year, preferably with regard to the stroke or stroke-like symptoms. Most preferably the functional outcome 3 months after the stroke or TIA is predicted. It is preferred in the context of the present invention, that the functional outcome is determined as ranking or the degree of severity of the outcome. The functional outcome may also be expressed in terms of need of nursing care or with respect to activities of daily living (ADL), e.g according to the Barthel Index, NIHSS and modified Ranking Scale.

"Reference expression profile" refers to the pattern of expression of a set of genes differentially expressed (i.e., overexpressed or underexpressed) in ischemia relative to a control (e.g., the expression level in an individual free of an ischemic event or the expression level of a stably expressed endogenous reference biomarker). A gene that is expressed at a level that is at least about 1.2-, 1.3-, 1.4-, 1.5-, 1.6-, 1.7-, 1.8-, 1.9-, 2.0-, 2.1-, 2.2-, 2.3-, 2.4-, 2.5-, 2.6-, 2.7-, 2.8-, 2.9, 3.0-, 3.1-, 3.2-, 3.3-, 3.4- or 3.5-fold higher than the level in a control is a gene overexpressed in ischemia and a gene from Tables 3 and 4 that is expressed at a level that is at least about 1.2-, 1.3-, 1.4-, 1.5-, 1.6-, 1.7-, 1.8-, 1.9-, 2.0-, 2.1-, 2.2-, 2.3-, 2.4, 2.5-, 2.6-, 2.7-, 2.8-, 2.9, 3.0-, 3.1-, 3.2-, 3.3-, 3.4- or 3.5-fold lower than the level in a control is a gene underexpressed in ischemia. Alternately, genes that are expressed at a level that is at least about 10%, 20%, 30%, 40%, 50%, 60%, 70%, 80%, 90%, or 100% higher than the level in a control is a gene overexpressed in ischemia and a gene that is expressed at a level that is at least about 10%, 20%, 30%, 40%, 50%, 60%, 70%, 80%, 90%, or 100% lower than the level in a control is a gene underexpressed in ischemia.

A "plurality" refers to two or more, for example, 2, 3, 4, 5, 6, 7, 8, 9, 10, 11, 12, 13, 14, 15, 16, 17, 18, 19, 20, 21, 22, 23 or more (e.g., genes). In some embodiments, a plurality refers to concurrent or sequential determination of about 15-85, 20-60 or 40-50 genes, for example, about 15, 20, 25, 30, 35, 40, 45, 50, 55, 60, 65, 70, 75, 80, 85, 90, 95 or 100, or more, genes. In some embodiments, "plurality" refers to all genes listed in one or more tables, e.g., all genes listed in Tables 3 and 4.

"Sample" or "biological sample" includes sections of tissues such as biopsy and autopsy samples, and frozen sections taken for histologic purposes. Such samples include blood, sputum, tissue, lysed cells, brain biopsy, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Array" as used herein refers to a solid support comprising attached nucleic acid or peptide probes. Arrays typically comprise a plurality of different nucleic acid or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., Science, 251:767-777 (1991). These arrays may generally be produced using mechanical synthesis methods or light directed synthesis methods which incorporate a combination of photolithographic methods and solid phase synthesis methods. Techniques for the synthesis of these arrays using mechanical synthesis methods are described in, e.g., U.S. Pat. No. 5,384,261. Arrays may comprise a planar surface or may be nucleic acids or peptides on beads, gels, polymeric surfaces, fibers such as fiber optics, glass or any other appropriate substrate as described in, e.g., U.S. Pat. Nos. 5,770,358, 5,789,162, 5,708,153, 6,040,193 and 5,800,992. Arrays may be packaged in such a manner as to allow for diagnostics or other manipulation of an all-inclusive device, as described in, e.g., U.S. Pat. Nos. 5,856,174 and 5,922,591.

The term "gene" means the segment of DNA involved in producing a polypeptide chain; it includes regions preceding and following the coding region (leader and trailer) as well as intervening sequences (introns) between individual coding segments (exons).

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

The phrase "stringent hybridization conditions" refers to conditions under which a probe will hybridize to its target subsequence, typically in a complex mixture of nucleic acid, but to no other sequences. Stringent hybridization conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent hybridization conditions are selected to be about 5-10° C. lower than the thermal melting point for the specific sequence at a defined ionic strength Ph. The Tm is the temperature (under defined ionic strength, Ph, and nucleic concentration) at which 50% of the probes complementary to the target hybridize to the target sequence at equilibrium (as the target sequences are present in excess, at Tm, 50% of the probes are occupied at equilibrium). Stringent hybridization conditions will be those in which the salt concentration is less than about 1.0 M sodium ion, typically about 0.01 to 1.0 M sodium ion concentration (or other salts) at Ph 7.0 to 8.3 and the temperature is at least about 30° C. for short probes (e.g., 10 to 50 nucleotides) and at least about 60° C. for long probes (e.g., greater than 50 nucleotides). Stringent hybridization conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent hybridization conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. "Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

Alanine (A), Glycine (G);

Aspartic acid (D), Glutamic acid (E);

Asparagine (N), Glutamine (Q);

Arginine I, Lysine (K);

Isoleucine (I), Leucine (L), Methionine (M), Valine (V);

Phenylalanine (F), Tyrosine (Y), Tryptophan (W);

Serine (S), Threonine (T); and

Cysteine (C), Methionine (M)

(see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region of an ischemia-associated gene (e.g., a gene set forth in Tables 3 and 4), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length, or over the full length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to ischemia-associated nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (on the internet at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

DETAILED DESCRIPTION

Introduction

The present invention is based, in part, on the discovery that gene expression profiles can distinguish stroke of atrial fibrillation etiology from arterial (large vessel) stroke or embolic stroke of undetermined source (ESUS).

Accordingly, the present invention is based, in part, on the discovery that RNA expression profiling can be used to differentiate stroke of atrial fibrillation etiology from arterial (large vessel) stroke or embolic stroke of undetermined source (ESUS). The genes identified herein to be associated with the occurrence of and/or risk of experiencing atrial fibrillation in ischemic stroke find use to diagnose atrial fibrillation in ischemic stroke based upon an RNA expression profile. The use of the presently identified gene allow for the use of a blood test for the rapid diagnosis of a cause of stroke.

In practice, the level of expression of genes associated with the occurrence or risk of atrial fibrillation in ischemic stroke can be measured in the blood of patients with an ischemic stroke. The expression of these genes can be assessed using any applicable method in the art, including, e.g., RT-PCR, NGS, microarrays or other technology. In various embodiments, the expression of these target genes can be normalized to internal control genes, which are known in the art. A panel of control genes that are specific for ischemic stroke have been developed and are quite reliable. The endogenous control genes have fairly constant expression over many age groups, different diseases, and both genders. Once the RNA expression levels of the target genes (i.e., atrial fibrillation in ischemic stroke-associated genes) are measured, and the RNA levels of the control genes are measured, then the target gene expression is normalized to the control genes. The expression levels of the normalized target genes can then be applied to a linear discriminant analysis model to predict whether the blood sample is from a patient who has experience or is at risk of experiencing atrial fibrillation in ischemic stroke and the probability that this is the case.

A blood test for the diagnosis of stroke is useful in several situations. For example, the gene expression panel can be used to predict whether atrial fibrillation in ischemic stroke is the cause of stroke in patients. In particular, it is important to diagnose disease that would guide appropriate disease treatment and management including determining the most effective treatments for stroke.

A diagnosis based on the expression levels of the presently identified atrial fibrillation in ischemic stroke-associated genes would guide appropriate treatment for stroke patients. The presently identified atrial fibrillation in ischemic stroke-associated genes further find use for diagnosing patients who have experienced or are at risk of experiencing Transient Ischemic Attacks. In these patients, the cause is often unknown. Thus, a blood test predicting the cause of the stroke could help prevent or ameliorate strokes in these patients.

Biomarkers Useful for the Prediction or Diagnosis of Atrial fibrillation in ischemic stroke, or for Distinguishing Atrial fibrillation in ischemic stroke from arterial (large vessel) stroke or embolic stroke of undetermined source (ESUS).

Biomarkers useful for the prediction, diagnosis or confirmation of the occurrence of atrial fibrillation in ischemic stroke, or for distinguishing atrial fibrillation in ischemic stroke from arterial (large vessel) stroke or embolic stroke of undetermined source (ESUS) (e.g., non-lacunar small deep infarct (SDI)) are selected from the group consisting of ELL2, GLIPR1, and MAPKAPK3. Determination of the expression levels of a plurality of the biomarkers of can be performed for the prediction, diagnosis or confirmation of the occurrence of atrial fibrillation in ischemic stroke in conjunction with other biomarkers known in the art for the prediction, diagnosis or confirmation of the occurrence of ischemic stroke, SDI and/or atrial fibrillation in ischemic stroke, in conjunction with biomarkers described herein and known in the art useful for determining the cause of ischemic stroke and/or in conjunction with methods known in the art for determining the cause of ischemic stroke.

Determination of the expression levels of a plurality of the biomarkers can be performed for the prediction, diagnosis or confirmation of the occurrence of stroke can also be performed independently, e.g., to diagnose that an atrial fibrillation in ischemic stroke has occurred, to distinguish atrial fibrillation in ischemic stroke from arterial (large vessel) stroke or embolic stroke of undetermined source (ESUS) or non-lacunar SDI, or to determine the risk that a patient may suffer an atrial fibrillation in ischemic stroke.

As appropriate, the expression levels of at least one or more biomarkers selected from the group consisting of ELL2, GLIPR1, and MAPKAPK3 are determined.

In some embodiments, the level of expression of biomarkers indicative of the occurrence of atrial fibrillation in ischemic stroke is determined within 72 hours, for example, within 60, 48, 36, 24, 12, 6 or 3 hours of a suspected ischemic event. An increased expression level of one or more atrial fibrillation in ischemic stroke-associated biomarkers selected from the group consisting of ELL2, GLIPR1, and MAPKAPK3, is correlative with or indicates that the patient suffers from or is at risk of developing atrial fibrillation in ischemic stroke. Conversely, a decreased expression level of one or more atrial fibrillation in ischemic stroke-associated biomarkers selected from the group consisting of ELL2, GLIPR1, and MAPKAPK3 is correlative with or indicates that the patient suffers from or is at risk of developing arterial (large vessel) stroke or embolic stroke of undetermined source (ESUS).

The overexpression or the underexpression of the biomarkers are determined with reference to a control level of expression. The control level of expression can be determined using any method known in the art. For example, the control level of expression can be from a population of individuals known to not have or be at risk for an ischemic event such as atrial fibrillation in ischemic stroke or can be determined with reference to a panel of stably expressed reference biomarkers. Also, threshold levels of expression can be determined based on levels of expression in predetermined populations (e.g., known to not have or be at risk for an ischemic event such as atrial fibrillation in ischemic stroke versus known to have or be at risk for atrial fibrillation in ischemic stroke). Overexpression or underexpression of a plurality of biomarkers that is at least about 1.2-fold, 1.3-fold, 1.4-fold, 1.5-fold, 1.6-fold, 1.7-fold, 1.8 fold, 1.9-fold, 2.0-fold, 2.1 fold, 2.2-fold, 2.3-fold, 2.4-fold, 2.5-fold, or more, in comparison to the expression levels of a plurality of stably expressed endogenous reference biomarkers, e.g., those listed in Table 1, is correlative with or indicates that the subject has experienced or is at risk of experiencing an atrial fibrillation in ischemic stroke.

Comparison to a Control Level of Expression

The expression levels of the atrial fibrillation in ischemic stroke-associated biomarkers are compared to a control level of expression. As appropriate, the control level of expression can be the expression level of the same atrial fibrillation in ischemic stroke-associated biomarker in an otherwise healthy individual (e.g., in an individual who has not experienced and/or is not at risk of experiencing a vascular event, e.g., TIA, ischemic stroke or a small deep infarct). In some embodiments, the control level of expression is the expression level of a plurality of stably expressed endogenous reference biomarkers, as described herein and/or known in the art. In some embodiments, the control level of expression is a predetermined threshold level of expression of the same atrial fibrillation in ischemic stroke-associated biomarker, e.g., based on the expression level of the biomarker in a population of otherwise healthy individuals. In some embodiments, the expression level of the atrial fibrillation in ischemic stroke-associated biomarker in the test subject and the expression level of the atrial fibrillation in ischemic stroke-associated biomarker in an otherwise healthy individual are normalized to (i.e., divided by), e.g., the expression levels of a plurality of stably expressed endogenous reference biomarkers.

In some embodiments, the overexpression or underexpression of an atrial fibrillation in ischemic stroke associated biomarker is determined with reference to the expression of the same atrial fibrillation in ischemic stroke associated biomarker in an otherwise healthy individual. For example, a healthy or normal control individual has not experienced and/or is not at risk of experiencing ischemic stroke, transient ischemic attack or a small deep infarction. The healthy or normal control individual generally has not experienced a vascular event (e.g., TIA, ischemic stroke, myocardial infarction, peripheral vascular disease, or venous thromboembolism) and does not have cerebral vascular disease. The healthy or normal control individual generally does not have one or more vascular risk factors (e.g., hypertension, diabetes mellitus, hyperlipidemia, or tobacco smoking). As appropriate, the expression levels of the target atrial fibrillation in ischemic stroke-associated biomarker in the healthy or normal control individual can be normalized (i.e., divided by) the expression levels of a plurality of stably expressed endogenous reference biomarkers.

In some embodiments, the overexpression or underexpression of an atrial fibrillation in ischemic stroke associated biomarker is determined with reference to one or more stably expressed endogenous reference biomarkers. Internal control biomarkers or endogenous reference biomarkers are expressed at the same or nearly the same expression levels in the blood of patients with stroke or TIAs or SDIs as compared to control patients. Target biomarkers are expressed at higher or lower levels in the blood of the stroke or TIA or SDI patients. The expression levels of the target biomarker to the reference biomarker are normalized by dividing the expression level of the target biomarker to the expression levels of a plurality of endogenous reference biomarkers. The normalized expression level of a target biomarker can be used to predict the occurrence or lack thereof of stroke or TIA or SDI, and/or the cause of stroke or TIA or SDI.

In some embodiments, the expression level of the atrial fibrillation in ischemic stroke-associated biomarker from a patient suspected of having or experiencing atrial fibrillation in ischemic stroke and from a control patient are normalized with respect to the expression levels of a plurality of stably expressed endogenous genes. The expression levels of the normalized expression of the atrial fibrillation in ischemic stroke-associated biomarker can be compared to the expression levels of the normalized expression of the same atrial fibrillation in ischemic stroke-associated biomarker in a control patient. The determined fold change in expression=normalized expression of target biomarker in atrial fibrillation in ischemic stroke patient/normalized expression of target biomarker in control patient. Overexpression or underexpression of the normalized atrial fibrillation in ischemic stroke-associated biomarker in the atrial fibrillation in ischemic stroke patient by at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of the normalized atrial fibrillation in ischemic stroke-associated biomarker in a healthy control patient is correlative with or indicates that the atrial fibrillation in ischemic stroke or SDI patient has experienced or is at risk of experiencing atrial fibrillation in ischemic stroke.

In some embodiments, the control level of expression is a predetermined threshold level. The threshold level can correspond to the level of expression of the same atrial fibrillation in ischemic stroke-associated biomarker in an otherwise healthy individual or a population of otherwise healthy individuals, optionally normalized to the expression levels of a plurality of endogenous reference biomarkers. After expression levels and normalized expression levels of the atrial fibrillation in ischemic stroke-associated biomarkers are determined in a representative number of otherwise healthy individuals and individuals predisposed to experiencing SDI or atrial fibrillation in ischemic stroke, normal and atrial fibrillation in ischemic stroke expression levels of the atrial fibrillation in ischemic stroke-associated biomarkers can be maintained in a database, allowing for determination of threshold expression levels indicative of the presence or absence of risk to experience atrial fibrillation in ischemic stroke or the occurrence of atrial fibrillation in ischemic stroke. If the predetermined threshold level of expression is with respect to a population of normal control patients, then overexpression or underexpression of the atrial fibrillation in ischemic stroke-associated biomarker (usually normalized) in the stroke patient by at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the threshold level is correlative with or indicates that the atrial fibrillation in ischemic stroke patient has experienced or is at risk of experiencing atrial fibrillation in ischemic stroke. If the predetermined threshold level of expression is with respect to a population of patients known to have experienced atrial fibrillation in ischemic stroke or known to be at risk for experiencing atrial fibrillation in ischemic stroke, then an expression level in the patient suspected of experiencing atrial fibrillation in ischemic stroke that is approximately equal to the threshold level (or overexpressed or underexpressed greater than the threshold level of expression), is correlative with or indicates that the atrial fibrillation in ischemic stroke or SDI patient has experienced or is at risk of experiencing atrial fibrillation in ischemic stroke.

With respect to the endogenous reference biomarkers used for comparison, preferably, Exemplary endogenous reference biomarkers that find use are listed in Table 1, below. Further suitable endogenous reference biomarkers are published, e.g., in Stamova, et al., BMC Medical Genomics (2009) 2:49. In some embodiments, the expression levels of a plurality of endogenous reference biomarkers are determined as a control. In some embodiments, the expression levels of at least about 2, 3, 4, 5, 6, 7, 8, 9, 10, 15, 20, 25, 30, 35, or more, endogenous reference biomarkers, e.g., as listed in Table 1 or known in the art, are determined as a control.

Table 1. The 38 endogenous reference biomarkers stably expressed in blood for use in normalization and as control levels.

TABLE 1

Stably expressed endogenous reference biomarkers

| Probe Set ID | Gene Symbol | Gene Title | GenBank ID | UniGene ID | RefSeq Transcript ID | RefSeq Protein ID |
|---|---|---|---|---|---|---|
| 201499_s_at | USP7 | ubiquitin specific peptidase 7 (herpes virus-associated) | NM_003470.1 | Hs.706830 | NM_003470 | NP_003461 |
| 202501_at | MAPRE2 | microtubule-associated protein, RP/EB family, member 2 | NM_014268.1 | Hs.532824 | NM_001143826 /// NM_001143827 /// NM_014268 /// NR_026570 | NP_001137298 /// NP_001137299 /// NP_055083 |
| 202573_at | CSNK1G2 | casein kinase 1, gamma 2 | AL530441 | Hs.651905 | NM_001319 | NP_001310 |
| 203280_at | SAFB2 | scaffold attachment factor B2 | NM_014649.1 | Hs.655392 | NM_014649 | NP_055464 |
| 204842_x_at | PRKAR2A | protein kinase, cAMP-dependent, regulatory, type II, alpha | BC002763.1 | Hs.631923 | NM_004157 | NP_004148 |
| 206138_s_at | PI4KB | phosphatidylinositol 4-kinase, catalytic, beta | NM_002651.1 | Hs.632465 | NM_002651 | NP_002642 |
| 207159_x_at | CRTC1 | CREB regulated transcription coactivator 1 | NM_025021.1 | Hs.371096 | NM_001098482 /// NM_015321 | NP_001091952 /// NP_056136 |
| 208630_at | HADHA | hydroxyacyl-Coenzyme A dehydrogenase/3-ketoacyl-Coenzyme A thiolase/enoyl-Coenzyme A hydratase (trifunctional protein), alpha subunit | AI972144 | Hs.516032 | NM_000182 | NP_000173 |
| 208786_s_at | MAP1LC3B | microtubule-associated protein 1 light chain 3 beta | AF183417.1 | Hs.356061 | NM_022818 | NP_073729 |
| 209192_x_at | KAT5 | K(lysine) acetyltransferase 5 | BC000166.2 | Hs.397010 | NM_006388 /// NM_182709 /// NM_182710 | NP_006379 /// NP_874368 /// NP_874369 |
| 210474_s_at | CDC2L1 /// CDC2L2 | cell division cycle 2-like 1 (PITSLRE proteins) /// cell division cycle 2-like 2 (PITSLRE proteins) | U04819.1 | Hs.651228 | NM_024011 /// NM_033486 /// NM_033487 /// NM_033488 /// NM_033489 /// NM_033492 /// NM_033493 /// NM_033529 | NP_076916 /// NP_277021 /// NP_277022 /// NP_277023 /// NP_277024 /// NP_277027 /// NP_277028 /// NP_277071 |

TABLE 1-continued

| Stably expressed endogenous reference biomarkers | | | | | | |
|---|---|---|---|---|---|---|
| Probe Set ID | Gene Symbol | Gene Title | GenBank ID | UniGene ID | RefSeq Transcript ID | RefSeq Protein ID |
| 211040_x_at | GTSE1 | G-2 and S-phase expressed 1 | BC006325.1 | Hs.386189 | NM_016426 | NP_057510 |
| 211289_x_at | CDC2L1 /// CDC2L2 | cell division cycle 2-like 1 (PITSLRE proteins) /// cell division cycle 2-like 2 (PITSLRE proteins) | AF067524.1 | Hs.651228 | NM_024011 /// NM_033486 /// NM_033487 /// NM_033488 /// NM_033489 /// NM_033492 /// NM_033493 /// NM_033529 | NP_076916 /// NP_277021 /// NP_277022 /// NP_277023 /// NP_277024 /// NP_277027 /// NP_277028 /// NP_277071 |
| 213311_s_at | TCF25 | transcription factor 25 (basic helix-loop-helix) | BF000251 | Hs.415342 | NM_014972 | NP_055787 |
| 214665_s_at | CHP | calcium binding protein P22 | AK000095.1 | Hs.406234 | NM_007236 | NP_009167 |
| 215063_x_at | LRRC40 | leucine rich repeat containing 40 | AL390149.1 | Hs.147836 | NM_017768 | NP_060238 |
| 215200_x_at | — | — | AK022362.1 | Hs.663419 | — | — |
| 215568_x_at | hCG_2003956 /// LYPLA2 /// LYPLA2P1 | hCG2003956 /// lysophospholipase II /// lysophospholipase II pseudogene 1 | AL031295 | Hs.533479 | NM_007260 /// NR_001444 | NP_009191 |
| 216038_x_at | DAXX | death-domain associated protein | BE965715 | Hs.336916 | NM_001141969 /// NM_001141970 /// NM_001350 /// NR_024517 | NP_001135441 /// NP_001135442 /// NP_001341 |
| 217393_x_at | UBE2NL | ubiquitin-conjugating enzyme E2N-like | AL109622 | Hs.585177 | NM_001012989 | NP_001013007 |
| 217549_at | — | — | AW574933 | Hs.527860 | — | — |
| 217672_x_at | EIF1 | eukaryotic translation initiation factor 1 | BF114906 | Hs.150580 | NM_005801 | NP_005792 |
| 217938_s_at | KCMF1 | potassium channel modulatory factor 1 | NM_020122.1 | Hs.654968 | NM_020122 | NP_064507 |
| 218378_s_at | PRKRIP1 | PRKR interacting protein 1 (IL11 inducible) | NM_024653.1 | Hs.406395 | NM_024653 | NP_078929 |
| 218571_s_at | CHMP4A | chromatin modifying protein 4A | NM_014169.1 | Hs.279761 | NM_014169 | NP_054888 |
| 219074_at | TMEM184C | transmembrane protein 184C | NM_018241.1 | Hs.203896 | NM_018241 | NP_060711 |
| 220052_s_at | TINF2 | TERF1 (TRF1)-interacting nuclear factor 2 | NM_012461.1 | Hs.496191 | NM_001099274 /// NM_012461 | NP_001092744 /// NP_036593 |
| 220411_x_at | PODNL1 | podocan-like 1 | NM_024825.1 | Hs.448497 | NM_001146254 /// NM_001146255 /// NM_024825 | NP_001139726 /// NP_001139727 /// NP_079101 |
| 221813_at | FBXO42 | F-box protein 42 | AI129395 | Hs.522384 | NM_018994 | NP_061867 |
| 222207_x_at | LOC441258 | Williams Beuren syndrome chromosome region 19 pseudogene | AK024602.1 | Hs.711232 | — | — |
| 222733_x_at | RRP1 | ribosomal RNA processing 1 homolog (*S. cerevisiae*) | BC000380.1 | Hs.110757 | NM_003683 | NP_003674 |
| 224667_x_at | C10orf104 | chromosome 10 open reading frame 104 | AK023981.1 | Hs.426296 | NM_173473 | NP_775744 |
| 224858_at | ZDHHC5 | zinc finger, DHHC-type containing 5 | AK023130.1 | Hs.27239 | NM_015457 | NP_056272 |

TABLE 1-continued

| Stably expressed endogenous reference biomarkers | | | | | | |
|---|---|---|---|---|---|---|
| Probe Set ID | Gene Symbol | Gene Title | GenBank ID | UniGene ID | RefSeq Transcript ID | RefSeq Protein ID |
| 225403_at | C9orf23 | chromosome 9 open reading frame 23 | AL528391 | Hs.15961 | NM_148178 /// NM_148179 | NP_680544 /// NP_680545 |
| 226253_at | LRRC45 | leucine rich repeat containing 45 | BE965418 | Hs.143774 | NM_144999 | NP_659436 |
| 227651_at | NACC1 | nucleus accumbens associated 1, BEN and BTB (POZ) domain containing | AI498126 | Hs.531614 | NM_052876 | NP_443108 |
| 232190_xat | LOC100133445 /// LOC115110 | hypothetical LOC100133445 /// hypothetical protein LOC115110 | AI393958 | Hs.132272 | NR_026927 /// XR_036887 /// XR_038144 | — |
| 49878_at | PEX16 | peroxisomal biogenesis factor 16 | AA523441 | Hs.100915 | NM_004813 /// NM_057174 | NP_004804 /// NP_476515 |

In some embodiments, the expression levels of the endogenous reference biomarkers GAPDH, ACTB, B2M, HMBS and PPIB are determined as a control. In some embodiments, the expression levels of 2, 3, 4, 5, 6, 7, 8, 9, 10, 15, 20, 25, or more, endogenous reference biomarkers selected from the group consisting of USP7, MAPRE2, CSNK1G2, SAFB2, PRKAR2A, PI4 KB, CRTC1, HADHA, MAP1LC3B, KATS, CDC2L1///CDC2L2, GTSE1, CDC2L1///CDC2L2, TCF25, CHP, LRRC40, hCG 2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHCS, C9orf23, LRRC45, NACC1, LOC100133445/// LOC115110, PEX16 are determined as a control.

Biomarkers indicative of atrial fibrillation in ischemic stroke have levels of expression that are at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of a plurality of stably expressed endogenous reference biomarkers, e.g., the geometric average expression level of the evaluated endogenous reference biomarkers, e.g., 2, 3, 4, 5, 6, 7, 8, 9, 10, 15, 20, 25, 30, 35, or more biomarkers listed in Table 1.

Methods of Detecting Biomarkers

Gene expression may be measured using any method known in the art. One of skill in the art will appreciate that the means of measuring gene expression is not a critical aspect of the invention. The expression levels of the biomarkers can be detected at the transcriptional or translational (i.e., protein) level.

In some embodiments, the expression levels of the biomarkers are detected at the transcriptional level. A variety of methods of specific DNA and RNA measurement using nucleic acid hybridization techniques are known to those of skill in the art (see, Sambrook, supra and Ausubel, supra) and may be used to detect the expression of the genes set forth herein.

Determining Gene Expression Level

The methods of the disclosure depend on the detection of differentially expressed genes for expression profiling across heterogeneous tissues. Thus, the methods depend on profiling genes whose expression in certain tissues is activated to a higher or lower level in an individual afflicted with a condition, for example, cancer, such as prostate cancer, relative to its expression in a non-cancerous tissues or in a control subject. Gene expression can be activated to a higher or lower level at different stages of the same conditions and a differentially expressed gene can be either activated or inhibited at the nucleic acid level or protein level, or may be subject to alternative splicing to result in a different polypeptide product. Such differences can be evidenced by a change in mRNA levels, surface expression, secretion or other partitioning of a polypeptide, for example. For the purpose of this disclosure, differential gene expression is considered to be present when there is at least about 1.1-fold, 1.2-fold, 1.3-fold, 1.4-fold, 1.5-fold, 1.6-fold, 1.7-fold, 1.8-fold, 1.9-fold, to two-fold.

Differential signature gene expression can be identified, or confirmed using methods known in the art such as qRT-PCR (quantitative reverse-transcription polymerase chain reaction) and microarray analysis. In particular embodiments, differential signature gene expression can be identified, or confirmed using microarray techniques. Thus, the signature genes can be measured in either fresh or paraffin-embedded tumor tissue, using microarray technology. In this method, polynucleotide sequences of interest are plated, or arrayed, on a microchip substrate. The arrayed sequences are then hybridized with specific DNA probes from cells or tissues of interest. In a preferred embodiment the technology combines fiber optic bundles and beads that self-assemble into an array. Each fiber optic bundle contains thousands to millions of individual fibers depending on the diameter of the bundle. Sensors are affixed to each bead in a given batch. The particular molecules on a bead define that bead's function as a sensor. To form an array, fiber optic bundles are dipped into pools of coated beads. The coated beads are drawn into the wells, one bead per well, on the end of each fiber in the bundle. The present disclosure is not limited to the solid supports described above. Indeed, a variety of other solid supports are contemplated including, but not limited to, glass microscope slides, glass wafers, gold, silicon, microchips, and other plastic, metal, ceramic, or biological surfaces. Microarray analysis can be performed by commercially available equipment, following manufacturer's protocols, such as by using Illumina's technology.

Exemplary arrays that are useful include, without limitation, a GeneChip® Human Transcriptome Array (HTA 2.0) and Clariom™ expression arrays available from ThermoFisher Scientific Inc., a Sentrix® Array or Sentrix® BeadChip Array available from Illumina®, Inc. (San Diego, Calif.) or others including beads in wells such as those described in U.S. Pat. Nos. 6,266,459, 6,355,431, 6,770,441, and 6,859,570; and PCT Publication No. WO 00/63437, each of which is hereby incorporated by reference. Other arrays having particles on a surface include those set forth in US 2005/0227252; US 2006/0023310; US 2006/006327; US 2006/0071075; US 2006/0119913; U.S. Pat. Nos. 6,489,606; 7,106,513; 7,126,755; 7,164,533; WO 05/033681; and WO 04/024328, each of which is hereby incorporated by reference.

An array of beads useful in the disclosure can also be in a fluid format such as a fluid stream of a flow cytometer or similar device. Exemplary formats that can be used in the disclosure to distinguish beads in a fluid sample using microfluidic devices are described, for example, in U.S. Pat. No. 6,524,793. Commercially available fluid formats for distinguishing beads include, for example, those used in XMAP™ technologies from Luminex or MPSS™ methods from Lynx Therapeutics.

Further examples of commercially available microarrays that can be used in the disclosure include, for example, an Illumina microarray or other microarray synthesized in accordance with techniques sometimes referred to as massively parallel sequencing technology known as next generation sequencing (NGS). Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. In still another embodiment, sequencing is paired-end sequencing. Optionally, an amplification step is performed prior to sequencing. As is known, complementary forward and reverse strands deriving from a single dsDNA molecule can be identified by their identical, or substantially identical unique sequence tags (i.e., barcodes or UMIs), and compared to identify, and correct for, amplification, library preparation, and sequencing based errors. In some embodiments, methods include analyzing next-generation sequencing (NGS) data for CNV detection using any one of several algorithms developed for each of the four broad methods for CNV detection using NGS, namely the depth of coverage (DOC), read-pair (RP), split-read (SR) and assembly-based (AS) methods. (Teo S. M., et al. Bioinformatics. 2012 Aug. 31). In some embodiments, methods include combining coverage with map information for the identification of deletions and duplications in targeted sequence data (Nord A. S., et al. BMC Genomics. 2011 Apr. 12; 12:184). As is well known in the art, various process in next generation sequencing can result in amplification, library preparation, and sequencing based errors. In some cases, complimentary forward and reverse sequences derived from a single dsDNA fragment can be matched based on identical, or substantially identical, unique sequence tags (i.e., barcodes or HMIs) and single nucleotide differences identified. In this manner, amplification, library preparation, and sequencing based errors can be identified and corrected.

Further examples of commercially available microarrays that can be used in the disclosure include, for example, an ThermoFisher Scientific Inc. (Affymetrix GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591, each of which is hereby incorporated by reference.

A spotted microarray can also be used in a method of the disclosure. An exemplary spotted microarray is a CodeLink™ Array available from Amersham Biosciences. Another microarray that is useful in the disclosure is one that is manufactured using inkjet printing methods such as SurePrint™ Technology available from Agilent Technologies. Other microarrays that can be used in the disclosure include, without limitation, those described in Butte, Nature Reviews Drug Discov. 1:951-60 (2002) or U.S. Pat. Nos. 5,429,807; 5,436,327; 5,561,071; 5,583,211; 5,658,734; 5,837,858; 5,919,523; 6,287,768; 6,287,776; 6,288,220; 6,297,006; 6,291,193; and 6,514,751; and WO 93/17126; WO 95/35505, each of which is hereby incorporated by reference.

DASL can be used for quantitative measurements of RNA target sequences as well as for DNA target sequences. DASL is described, for example, in Fan et al., Genome Res. 14:878-85 (2004); US 2003/0108900 and US 2004/0259105, each of which is incorporated herein by reference. Notably, the sensitivity of DASL using RNA from paraffin samples is about 80% compared to the assay using RNA prepared from fresh frozen samples, with results up to 90% sensitivity observed. Gene expression can be monitored and compared in formalin-fixed, paraffin-embedded clinical samples archived for more than 5 years.

The expression patterns for signature genes are determined based on quantitative detection of nucleic acids or oligonucleotides corresponding to the signature genes, which means at least two nucleotides covalently linked together. Thus, the disclosure also provides a collection of nucleic acids and oligonucleotides that correspond to a signature gene or a set of signature genes. A nucleic acid useful in the methods of the disclosure will generally contain phosphodiester bonds, although in some cases, nucleic acid analogs are included that may have alternate backbones, including, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. Modifications of the ribose-phosphate backbone may be done to facilitate the addition of labels, or to increase the stability and half-life of such molecules in physiological environments. Nucleic acid analogs can find use in the methods of the disclosure as well as mixtures of naturally occurring nucleic acids and analogs.

The nucleic acids corresponding to signature genes can be single stranded or double stranded, as specified, or contain portions of both double stranded or single stranded sequence. The nucleic acid can be DNA, both genomic and cDNA, RNA or a hybrid, where the nucleic acid contains any combination of deoxyribo- and ribo-nucleotides, and any combination of bases, including, for example, uracil, adenine, thymine, cytosine, guanine, inosine, xanthine hypoxanthine, isocytosine, isoguanine. A nucleic acid sequence corresponding to a signature gene can be a portion of the gene, a regulatory sequence, genomic DNA, cDNA, RNA including mRNA and rRNA, or others.

A nucleic acid sequence corresponding to a signature gene can be derived from the tissue sample, or from a secondary source such as a product of a reaction such as, for example, a detection sequence from an invasive cleavage reaction, a ligated probe from an OLA or DASL reaction, an extended probe from a PCR reaction, or PCR amplification product, ("amplicon"). Exemplary methods for preparing secondary probes from target sequences are described in US 2003/0108900; US 2003/0170684; US 2003/0215821; US 2004/0121364; and US 2005/0181394. Thus, a nucleic acid sequence corresponding to a signature gene can be derived from the primary or from a secondary source of nucleic acid.

As will be appreciated by those in the art, a complementary nucleic acid sequence useful in the methods of the disclosure can take many forms and probes are made to hybridize to nucleic acid sequences to determine the presence or absence of the signature gene in a sample. In a preferred embodiment, a plurality of nucleic acid sequences is detected. As used herein, "plurality" or grammatical equivalents herein refers to at least 2, 10, 20, 25, 50, 100 or 200 different nucleic sequences, while at least 500 different nucleic sequences is preferred. More preferred is at least 1000, with more than 5000 or 10,000 particularly preferred and more than 50,000 or 100,000 most preferred. Detection can be performed on a variety of platforms such as those set forth above or in the Examples.

The expression level of a signature gene in a tissue sample can be determined by contacting nucleic acid molecules derived from the tissue sample with a set of probes under conditions where perfectly complementary probes form a hybridization complex with the nucleic acid sequences corresponding to the signature genes, each of the probes including at least two universal priming sites and a signature gene target-specific sequence; amplifying the probes forming the hybridization complexes to produce amplicons; and detecting the amplicons, wherein the detection of the amplicons indicates the presence of the nucleic acid sequences corresponding to the signature gene in the tissue sample; and determining the expression level of the signature gene.

In the context of the present disclosure, multiplexing refers to the detection, analysis, or amplification of a plurality of nucleic acid sequences corresponding to the signature genes. In one embodiment multiplex refers to the number of nucleic acid sequences corresponding to a signature gene to be analyzed in a single reaction, vessel or step. The multiplexing method is useful for detection of a single nucleic acid sequence corresponding to a signature gene as well as a plurality of nucleic acid sequences corresponding to a set of signature genes. In addition, as described below, the methods of the disclosure can be performed simultaneously and in parallel in a large number of tissue samples.

The expression level of nucleic acid sequences corresponding to a set of signature genes in a tissue sample can be determined by contacting nucleic acid molecules derived from the tissue sample with a set of probes under conditions where complementary probes form a hybridization complex with the signature gene-specific nucleic acid sequences, each of the probes including at least two universal priming sites and a signature gene-specific nucleic acid sequence; amplifying the probes forming the hybridization complexes to produce amplicons; detecting the amplicons, wherein the detection of the amplicons indicates the presence of the nucleic acid sequences corresponding to the set of signature genes in the tissue sample; and determining the expression level of the target sequences, wherein the expression of at least two, at least three, at least five signature gene-specific sequences is detected.

The presence of one, two or a plurality of nucleic acid sequences corresponding to a set of signature genes can be determined in a tissue sample using single, double or multiple probe configurations. The methods of the disclosure can be practiced with tissue samples having substantially degraded nucleic acids. Although methods for pre-qualifying samples with respect to nucleic acid degradation are described above, those skilled in the art will recognize that other detection methods described herein or known in the art can be used to detect RNA levels in a sample suspected of having degraded nucleic acids, thereby determine the level of nucleic acid degradation in accordance with the disclosure.

The present disclosure particularly draws on methodologies outlined in US 2003/0215821; US 2004/0018491; US 2003/0036064; US 2003/0211489, each of which is expressly incorporated by reference in their entirety. In addition, universal priming methods are described in detail in US 2002/0006617; US 2002/0132241, each of which is expressly incorporated herein by reference. In addition, multiplex methods are described in detail US 2003/0211489; US 2003/0108900, each of which is expressly incorporated herein by reference. In general, the methods of the disclosure can be performed in a variety of ways, as further described below and in the cited applications incorporated by reference. For example, mRNA signature samples can initially be subjected to a "complexity reduction" step, whereby the presence of a particular target is confirmed by adding probes that are enzymatically modified in the presence of the signature gene-specific nucleic acid sequence. The modified probes are then amplified and detected in a wide variety of ways. Preferred embodiments draw on multiplexing methods, which allow for the simultaneous detection of a number of nucleic acid sequences, for example, corresponding to a set of signature genes, as well as multiplexing amplification reactions, for example by using universal priming sequences to do multiplex PCR reactions. If desired, the initial step also can be both a complexity reduction and an amplification step.

The randomly ordered BeadArray™ technology (Michael et al., Anal Chem 70, 1242-8 (1998); Walt, Science 287, 451-2 (2000)) has been developed at Illumina as a platform for SNP genotyping (Fan et al., Cold Spring Harb Symp Quant Biol 68:69-78 (2003); Gunderson et al., Nat Genet 37:549-54 (2005)), gene expression profiling (Bibikova et al. Am J Pathol 165:1799-807 (2004); Fan et al., Genome Res 14:878-85 (2004); Kuhn et al., Genome Res 14:2347-56 (2004); Yeakley et al., Nat Biotechnol 20:353-8 (2002)) and DNA methylation detection (Bibikova et al., Genome Res 16:383-93 (2006)). Each array was assembled on an optical fiber bundle consisting of about 50,000 individual fibers fused together into a hexagonally packed matrix. The ends of the bundle were polished, and one end was chemically etched to create a microscopic well in each fiber. These wells were each filled with a 3-micron diameter silica bead. Each derivatized bead had several hundred thousand copies of a particular oligonucleotide covalently attached and available for hybridization. Bead libraries were prepared by conjugation of oligonucleotides to silica beads, followed by quantitative pooling together of the individual bead types. Because the beads were positioned randomly on the array, a decoding process was carried out to determine the location and identity of each bead in every array location (Gunderson et al., Genome Res 14: 870-7 (2004)). Each of the 1,624 bead types in the resulting universal array was present at an average redundancy of about 30. Consequently, each assay measurement was the result of data averaged from multiple beads, which increased precision and greatly reduced the possibility of error.

To further increase sample throughput, the arrays were formatted into a matrix, in a pattern that matched the wells of standard 96-well microtiter plates. The matrix format allows streamlined sample handling. By bringing the array to the sample (literally dipping it into the microtiter well), sample and array processing is simplified and integrated for handling of 96 separate samples simultaneously.

A flexible, sensitive, accurate and cost-effective gene expression profiling assay, the DASL (for DNA-mediated annealing, selection, extension and ligation) assay, can be used for parallel analysis of thousands of sequence targets. In this assay in one embodiment, two oligos were designed to target a specific gene sequence. Total RNA was first converted to cDNA by random priming. The corresponding query oligos hybridized to the cDNA, and were extended and ligated enzymatically. The ligated products were then amplified and fluorescently labeled during PCR, and finally detected by binding to address sequences on the universal array. The hybridization intensity was used as a measurement of the original mRNA abundance in the sample.

Unlike most of the other array technologies that use an in vitro transcription (IVT)-mediated sample labeling procedure (Phillips and Eberwine, Methods 10, 283-8 (1996)), DASL uses random priming in the cDNA synthesis, and therefore does not depend on an intact poly-A tail for T7-oligo-d(T) priming. In addition, the assay utilizes a relatively short target sequence of about 50 nucleotides for query oligonucleotide annealing, thus allowing microarray analyses of degraded RNAs (Bibikova et al., Am J Pathol 165:1799-807 (2004); Bibikova et al., Clin Chem 50:2384-6 (2004)).

Software developed at Illumina can be used for automatic image registration (Galinsky, Bioinformatics 19:1832-6 (2003)) and extraction of feature intensities. Briefly, the feature extraction algorithm represents a weighted 6.times.6 average of pixel intensities. The outlier algorithm was implemented at the feature level (each probe sequence was represented by 30 features on average) to remove features that fell outside of a robust confidence interval of the median response. Array data can be normalized using the "rank invariant" method in Illumina's BeadStudio software.

Providing Appropriate Treatment and Prevention Regimes to Patient

Upon a positive determination or confirmation that a patient has experienced a stroke, and a determination of the cause of stroke, e.g., using the biomarkers provided herein, the methods further provide for the step of prescribing, providing or administering a regime for the prophylaxis or treatment of ischemic stroke or SDI. By diagnosing the occurrence and/or the cause of stroke using the biomarkers described herein, a patient can rapidly receive treatment that is tailored to and appropriate for the type of stroke that has been experienced, or that the patient is at risk of experiencing.

In cases where arterial (large vessel) stroke or embolic stroke of undetermined source (ESUS) is indicated, further evaluation to the cause of arterial (large vessel) stroke or embolic stroke of undetermined source (ESUS) can be performed.

For example, if the expression levels of the plurality of ischemic stroke-associated biomarkers indicate the occurrence or risk of ischemic stroke, a positive diagnosis of ischemic stroke can be supported or confirmed using methods known in the art. For example, the patient can be subject to MRI imaging of brain and vessels, additional blood tests, EKG, and/or echocardiogram.

If the expression levels of the plurality of biomarkers indicate the occurrence or risk of cardioembolic stroke, the patient can be prescribed or administered a regime of an anticoagulant.

If the expression levels of the plurality of biomarkers indicate the occurrence or risk of carotid stenosis, the patient can be prescribed or administered a regime of an anti-platelet drug. The most frequently used anti-platelet medication is aspirin. An alternative to aspirin is the anti-platelet drug clopidogrel (Plavix). Some studies indicate that aspirin is most effective in combination with another anti-platelet drug. In some embodiments, the patient is prescribed a combination of low-dose aspirin and the anti-platelet drug dipyridamole (Aggrenox), to reduce blood clotting. Ticlopidine (Ticlid) is another anti-platelet medication that finds use. Patients having a moderately or severely narrowed neck (carotid) artery, may require or benefit from carotid endarterectomy. This preventive surgery clears carotid arteries of fatty deposits (atherosclerotic plaques) to prevent a first or subsequent strokes. In some embodiments, the patient may require or benefit from carotid angioplasty, or stenting. Carotid angioplasty involves using a balloon-like device to open a clogged artery and placing a small wire tube (stent) into the artery to keep it open.

If the expression levels of the plurality of biomarkers indicate the occurrence or risk of atrial fibrillation, the patient can be prescribed a regime of an anti-coagulant (to prevent stroke) and/or a pharmacological agent to achieve rate control. Exemplary anticoagulants include aspirin, heparin, warfarin, and dabigatran. Exemplary rate control drugs include beta blockers (e.g., metoprolol, atenolol, bisoprolol), non-dihydropyridine calcium channel blockers (e.g., diltiazem or verapamil), and cardiac glycosides (e.g., digoxin).

If the expression levels of the plurality of biomarkers indicate the occurrence or risk of transient ischemic attacks (TIA), the patient can be prescribed a regime of medications and/or life-style adjustments (e.g., diet, exercise, stress) to minimize risk factors can be recommended, including reducing blood pressure and cholesterol levels, and controlling diabetes. Several medications to decrease the likelihood of a stroke after a transient ischemic attack. The medication selected will depend on the location, cause, severity and type of TIA, if TIA has occurred. For example, the patient may be prescribed a regime of an anti-platelet drug. The most frequently used anti-platelet medication is aspirin. An alternative to aspirin is the anti-platelet drug clopidogrel (Plavix). Some studies indicate that aspirin is most effective in combination with another anti-platelet drug. In some embodiments, the patient is prescribed a combination of low-dose aspirin and the anti-platelet drug dipyridamole (Aggrenox), to reduce blood clotting. Ticlopidine (Ticlid) is another anti-platelet medication that finds use to prevent or reduce the risk of stroke in patients who have experienced TIA. In some embodiments, the patient may be prescribed a regime of an anticoagulant. Exemplary anticoagulants include aspirin, heparin, warfarin, and dabigatran. Patients having a moderately or severely narrowed neck (carotid) artery, may require or benefit from carotid endarterectomy to clear carotid arteries of fatty deposits (atherosclerotic plaques) before another TIA or stroke can occur. In some embodiments, the patient may require or benefit from carotid angioplasty, or stenting.

The present methods for determining whether a patient has experienced or has a predisposition to experience atrial fibrillation in ischemic stroke can be confirmed, complemented by, and/or used in conjunction with diagnostic tests known in the art for diagnosing atrial fibrillation in ischemic stroke. For example, the present methods can be performed in conjunction with additional diagnostic based on imaging or ultrasound techniques. In various embodiments, the present methods are performed in conjunction with one or more diagnostic tests selected from the group consisting of X-ray computed tomography (CT), magnetic resonance imaging (MRI) brain scanning, vascular imaging of the head and neck with doppler or magnetic resonance angiography (MRA), CT angiography (CTA), electrocardiogram (e.g., EKG or ECG), cardiac ultrasound and cardiac monitoring. In various embodiments, the patient is subjected to cardiac monitoring for at least 2 days, e.g., for 2-30 days or for 7-21 days, e.g., for 2, 5, 7, 10, 12, 14, 18, 20, 21, 25, 28, 30, or more days, as appropriate. An infarction located in a subcortical region of the brain is associated with or correlated with a diagnosis of atrial fibrillation in ischemic stroke. An infarction located in a cortical region of the brain, e.g., in regions of the penetrating arteries, e.g., basal ganglia, thalamus, internal capsule, corona radiata and/or pons, is associated with or correlated with a diagnosis of arterial (large vessel) stroke or embolic stroke of undetermined source (ESUS). In some embodiments, the size of the infarction is determined.

Solid Supports and Kits

The invention further provides, a solid support comprising a plurality of nucleic acid probes that hybridize to a plurality (e.g., two or more, or all) of the genes set forth above, and optionally Table 1. For example, the solid support can be a microarray attached to a plurality of nucleic acid probes that hybridize to a plurality (e.g., two or more, or all) of the biomarkers are selected from ELL2, GLIPR1, and MAPKAPK3 and optionally Table 1. In various embodiments, the solid supports are configured to exclude genes not associated with or useful to the diagnosis, prediction or confirmation of an atrial fibrillation in ischemic stroke, or for stroke generally. For example, genes that are overexpressed or underexpressed less than 1.2-fold in subjects with atrial fibrillation in ischemic stroke in comparison to a control level of expression can be excluded from the present solid supports. In some embodiments, genes that are overexpressed or underexpressed less than 1.2-fold in subjects with ischemic stroke, including atrial fibrillation in ischemic stroke, cardioembolic stroke, atherothrombotic stroke, TIA, and stroke subsequent to atrial fibrillation, in comparison to a control level of expression can be excluded from the present solid supports. The solid support may optionally further comprise a plurality of nucleic acid probes that hybridize to a plurality (e.g., two or more, or all) of the genes useful for the diagnosis of ischemic stroke, cardioembolic stroke, carotid stenosis, and/or atrial fibrillation, as described herein. The solid support may be a component in a kit.

In addition, the kit can comprise appropriate buffers, salts and other reagents to facilitate amplification and/or detection reactions (e.g., primers, labels) for determining the expression levels of a plurality of the genes above. In one embodiment, the kit comprises appropriate buffers, salts and other reagents to facilitate amplification and/or detection reactions (e.g., primers, labels) for determining the expression levels of a plurality of the genes set forth above. In one embodiment, the kit comprises appropriate buffers, salts and other reagents to facilitate amplification and/or detection reactions (e.g., primers) for determining the expression levels of a plurality of the genes. In one embodiment, the kit further comprises appropriate buffers, salts and other reagents to facilitate amplification and/or detection reactions (e.g., primers) for determining the expression levels of a plurality of the genes useful for the diagnosis of ischemic stroke, cardioembolic stroke, carotid stenosis, atrial fibrillation, and/or transient ischemic attacks (TIA), as described herein. The kits can also include written instructions for the use of the kit.

In one embodiment, the kits comprise a plurality of antibodies that bind to a plurality of the biomarkers set forth above. The kits may further comprise a plurality of antibodies that bind to a plurality of the biomarkers useful for the diagnosis of ischemic stroke, cardioembolic stroke, carotid stenosis, atrial fibrillation, and/or transient ischemic attacks (TIA), as described herein. The antibodies may or may not be immobilized on a solid support, e.g., an ELISA plate.

In a further aspect of the present invention, a pharmaceutical pack (kit) is provided, the pack comprising a therapeutic agent and a set of instructions for administration of the therapeutic agent to humans diagnostically tested for one or more variants of the present invention, as disclosed herein. The therapeutic agent can be a small molecule drug, an antibody, a peptide, an antisense or rnai molecule, or other therapeutic molecules. In one embodiment, an individual identified as a carrier of at least one variant of the present invention is instructed to take a prescribed dose of the therapeutic agent. In one such embodiment, an individual identified as a homozygous carrier of at least one variant of the present invention is instructed to take a prescribed dose of the therapeutic agent. In another embodiment, an individual identified as a non-carrier of at least one variant of the present invention is instructed to take a prescribed dose of the therapeutic agent.

In certain embodiments, the kit further comprises a set of instructions for using the reagents comprising the kit. In certain embodiments, the kit further comprises a collection of data comprising correlation data between the polymorphic markers assessed by the kit and susceptibility to prostate cancer and/or colorectal cancer.

Therapeutic Agents

Treatment of Atrial Fibrillation and Atrial flutter is generally directed by two main objectives: (i) to prevent stroke and (ii) to treat symptoms.

(i) Stroke Prevention

Anticoagulation is the therapy of choice for stroke prevention in atrial fibrillation and is indicated for the majority of patients with this arrhythmia. The only patients for whom anticoagulation is not strongly recommended are those younger than 65 years old who are considered low-risk, i.e., they have no organic heart disease, no hypertension, no previous history of stroke or transient ischemic attacks and no diabetes. This group as a whole has a lower risk of stroke and stroke prevention with aspirin is generally recommended. For all other patients, anticoagulation is indicated whether the atrial fibrillation is permanent, recurrent paroxysmal or recurrent persistent. It cannot be generalized how patients who present with their first episode of paroxysmal atrial fibrillation should be treated and the decision needs to be individualized for each patient. Anticoagulation is also indicated even when the patient with atrial fibrillation is felt to be maintained in sinus rhythm with antiarrhythmic therapy (rhythm controlled) since this type of therapy does not affect stroke risk.

Anticoagulation is recommended in atrial fibrillation, as detailed above, for prevention of cardioembolism and stroke. The most widely studied oral anticoagulant is warfarin and this medication is universally recommended for chronic oral anticoagulation in atrial fibrillation. Warfarin has few side effects aside from the risk of bleeding but requires regular and careful monitoring of blood values during therapy (to measure the effect of the anticoagulation). The oral anticoagulant ximelagatran showed promise in stroke prevention in patients with atrial fibrillation and had the advantage of not requiring regular monitoring like warfarin. Ximelagatran was found however to cause unexplained liver injury and was withdrawn from the market in 2006. Several agents are available for intravenous and/or subcutaneous therapy, including heparin and the low molecular weight heparins (e.g., enoxaparin, dalteparin, tinzaparin, ardeparin, nadroparin and reviparin). These medications are recommended when rapid initiation of anticoagulation is necessary or if oral anticoagulation therapy has to be interrupted in high risk patients or for longer than one week in other patients for example due to a series of procedures. Other parenteral anticoagulants are available but not specifically recommended as therapy in atrial fibrillation; e.g., the factor Xa inhibitors fondaparinux and idraparinux, the thrombin-inhibitors lepirudin, bivalirudin and argatroban as well as danaparoid.

In another aspect, the pharmaceutical composition comprising one or more ASIC1a inhibitors further includes one or more anti-clotting agents. Anti-clotting agents for use in the present application include antiplatelet agents, anticoagulant agents, anti-arrhythmic agents, or a combination thereof. Use of these anti-clotting agents may further increase the prophylactic and/or therapeutic efficacy of the ASIC1a inhibitor(s) administered to a subject in need thereof, either combinatorially or synergistically.

In one embodiment, the pharmaceutical composition further includes one or more antiplatelet agents. Exemplary antiplatelet agents include, but are not limited to COX inhibitors, adenosine diphosphate (ADP) receptor inhibitors, phosphodiesterase inhibitors, Glycoprotein IIb/IIIa inhibitors, adenosine reuptake inhibitors, thromboxane inhibitors, and combinations thereof. Some of the antiplatelet agents have multiple modes of action as reflected in the lists below.

COX inhibitors include acetylsalicylic acid (e.g., Aspirin) and triflusal (e.g., Disgren, Grendis, Aflen and Triflux), which irreversibly inhibit the COX-1 enzyme, prostaglandin-endoperoxide synthase-1 (i.e., COX-1 or PTGS1) and modify the enzymatic activity of the COX-2 enzyme (i.e., COX-2 or PTGS2), as well reversible COX-2 inhibitors targeting COX-2/PTGS2, such as celecoxib (e.g., Celebrex).

Adenosine diphosphate (ADP) receptor inhibitors for use in the present application include reversible or irreversible anatagonists of P2Y12 ADP receptors. Exemplary ADP receptor inhibitors include thienopyridines, such as the irreversible P2Y12 inhibitors, prasugrel, clopidogrel (e.g., Plavix), and reversible $P2PY_{12}$ inhibitors, such as ticagrelor (e.g., Brilinta).

Phosphodiesterase inhibitors for use in the present application include, but are not limited to dipyridamole (e.g., Persantine), cilostazol (e.g., Pletal), triflusal (e.g., Disgren, Grendis, Aflen and Triflux), and vorapaxar (e.g., Zontivity).

Glycoprotein IIb/IIIa inhibitors for use in the present application include, but are not limited to abciximab (e.g., ReoPro), eptifibatide (e.g., Integrilin), ifetroban, iloprost, isocarbacyclin methyl ester, itazigrel, lamifiban, lifarizine, molsidomine, nifedipine, orbofiban, oxagrelate, roxifiban, and tirofiban (Aggrastat).

Adenosine reuptake inhibitors for use in the present application include, but are not limited to acadesine, acetate, barbiturates, benzodiazepines, calcium channel inhibitors, carbamazepine, carisoprodol, cilostazol (Pletal), cyclobenzaprine, dilazep, estradiol, ethanol, flumazenil, hexobendine, hydroxyzine, indomethacin, inosine, KF24345, meprobamate, nitrobenzylthioguanosine, nitrobenzylthioinosine, papaverine, pentoxifylline, phenothiazines, phenytoin, progesterone, propentofylline, propofol, puromycin, R75231, RE 102 BS, soluflazine, toyocamycin, tracazolate, and tricyclic antidepressants.

Thromboxane inhibitors for use in the present application inhibit the synthesis of thromboxane and/or inhibit the target effect of thromboxane. Exemplary thromboxane inhibitors include, but are not limited to acetylsalicylic acid (e.g., Aspirin), dipyridamole, ifetroban, naproxen, picotamide, ridogrel, sulotroban, terutroban, ticlopidine, trapidil, triclopidine, trifenagrel, trifusal (e.g., Disgren, Grendis, Aflen and Triflux), and trilinolein.

In another embodiment, the pharmaceutical composition further includes one or more anticoagulant agents. In a particular embodiment, the anticoagulant agent is a vitamin-K epoxide reductase inhibitor. In other embodiments, the anticoagulant agent is a direct Factor Xa inhibitor, an indirect Factor Xa inhibitor, a direct thrombin inhibitor, or an indirect thrombin inhibitor (which are collectively known as direct oral anticoagulants (DOACs) or non-VKA oral anticoagulants). Vitamin K-epoxide reductase inhibitors for use in combination with the ASIC1a inhibitors of the present application include 4-hydroxycoumarin derivatives and 1,3-indandione derivatives. Exemplary vitamin K epoxide reductase inhibitors include, but are not limited to acenocoumarol (e.g., Sintrom and Sinthrome), anisindione, clorindione, coumarin, coumadin (e.g., warfarin), dicumarol and its derivatives (e.g., bis-hydroxycoumarin, bishydroxycoumarin, dicoumarin, dicoumarol), disulfiram, ethyl biscoumacetate, N-ethylmaleimide, fluindione, phenindione (e.g., Dindevan), phenprocoumon (e.g., Marcoumar, Marcumar and Falithrom), 1-N-methyl-5-thiotetrazole, 5,5'-dithiobis(1-methyltetrazole), pharmaceutically acceptable salts and solvates thereof, and combinations thereof.

Non-VKA oral anticoagulants (NOACs) for use in the present application include direct factor Xa inhibitors, such as apixaban (e.g., Eliquis), edoxaban (e.g., Savaysa, Lixiana), rivaroxaban (e.g., Xarelto), betrixaban (e.g., Bevyxxa), and YM466; direct thrombin inhibitors (or factor IIa inhibitors), such as AZD-0837, dabigatran (e.g., Pradaxa, Pradax, and Prazaxa), ximelagatran (e.g., Exanta), and melagatran, the active form of ximelagatran; indirect factor Xa inhibitors, such as fondaparinux (e.g., Arixtra), ultralow molecular weight heparin (ULMWH); indirect thrombin inhibitors, such as heparin, antithrombin, heparin in combination with antithrombin, enoxaparin (e.g., Lovenox), low molecular weight heparin (LMWH), dalteparin sodium (e.g., Fragmin), batroxobin, and hementin; including salts and solvates thereof, and combinations thereof.

In another embodiment, the pharmaceutical composition for use in the present application further includes one or more anti-arrhythmic agents. Exemplary anti-arrhythmic agents include amiodarone, AZD-1305, budiodarone, celivarone, dofetilide, dronedarone, ibutilide, flecainide, propafenone, quinidine, sotolol, vernakalant, and combinations thereof.

Any single, plurality, or combination of anticoagulants, salts thereof, solvates thereof, and derivatives thereof, may be used for modulating anticoagulant function, including other anticoagulants not mentioned here without departing from the present application.

(ii) Symptom Control. Medical and surgical therapy applied to control symptoms of atrial fibrillation is tailored to the individual patient and consists of heart rate and/or rhythm control with medications, radiofrequency ablation and/or surgery.

Antiarrhythmic medications. In general terms, antiarrhythmic agents are used to suppress abnormal rhythms of the heart that are characteristic of cardiac arrhythmias, including atrial fibrillation and atrial flutter. One classification of antiarrhythmic agents is the Vaughan Williams classification, in which five main categories of antiarrhythmic agents are defined. Class I agents are fast sodium channel blockers and are subclassified based on kinetics and strength of blockade as well as their effect on repolarization. Class Ia includes disopyramide, moricizine, procainamide and quinidine. Class Ib agents are lidocaine, mexiletine, tocamide, and phenyloin. Class Ic agents are encamide, flecamide, propafenone, ajmaline, cibenzoline and detajmium. Class II agents are beta blockers, they block the effects of catecholamines at beta-adrenergic receptors. Examples of beta blockers are esmolol, propranolol, metoprolol, alprenolol, atenolol, carvedilol, bisoprolol, acebutolol, nadolol, pindolol, labetalol, oxprenotol, penbutolol, timolol, betaxolol, cartelol, sotalol and levobunolol. Class III agents have mixed properties but are collectively potassium channel blockers and prolong repolarization. Medications in this category are amiodarone, azimilide, bretylium, dofetilide, tedisamil, ibutilide, sematilide, sotalol, N-acetyl procainamide, nifekalant hydrochloride, vernakalant and ambasilide. Class IV agents are calcium channel blockers and include verapamil, mibefradil and diltiazem. Finally, class V consists of miscellaneous antiarrhythmics and includes digoxin and adenosine.

Pharmacologic measures for maintenance of heart rate control include beta blockers, calcium channel blockers and digoxin. All these medications slow the electrical conduction through the atrioventricular node and slow the ventricular rate response to the rapid atrial fibrillation. Some antiarrhythmics used primarily for rhythm control (see below) also slow the atrioventricular node conduction rate and thus the ventricular heart rate response. These include some class III and Ic medications such as amiodarone, sotalol and flecamide.

Cardioversion. Cardioversion of the heart rhythm from atrial fibrillation or atrial flutter to sinus rhythm can be achieved electrically, with synchronized direct-current cardioversion, or with medications such as ibutilide, amiodarone, procainamide, propafenone and flecamide.

Heart Rhythm Control

Atrial fibrillation (AF) is an abnormal heart rhythm (cardiac arrhythmia) which involves the two small, upper heart chambers (the atria). Heart beats in a normal heart begin after electricity generated in the atria by the sinoatrial node spreads through the heart and causes contraction of the heart muscle and pumping of blood. In AF, the regular electrical impulses of the sinoatrial node are replaced by disorganized, rapid electrical impulses, which result in irregular heartbeats. AF is an important risk factor for stroke, the most feared complication of atrial fibrillation.

The symptoms of atrial fibrillation may be treated with medications which slow the heart rate. Several medications as well as electrical cardioversion may be used to convert AF to a normal heart rhythm. Surgical and catheter-based therapies may also be used to prevent atrial fibrillation in certain individuals. People with AF are often given blood thinners such as warfarin to protect them from strokes.

Atrial fibrillation is usually accompanied by symptoms related to either rapid heart rate or embolization. Rapid and irregular heart rates may be perceived as palpitations, exercise intolerance, and occasionally produce angina and congestive symptoms of shortness of breath or edema. Sometimes the arrhythmia will be identified with the onset of a stroke or a transient ischemic attack (TIA). It is not uncommon to identify atrial fibrillation on a routine physical examination or electrocardiogram (ECG/EKG), as it may be asymptomatic in some cases.

Paroxysmal atrial fibrillation is the episodic occurrence of the arrhythmia and may be difficult to diagnose. Episodes may occur with sleep or with exercise, and their episodic nature may require prolonged ECG monitoring (e.g., a Holter monitor) for diagnosis.

Atrial fibrillation is diagnosed on an electrocardiogram, an investigation performed routinely whenever irregular heartbeat is suspected. Characteristic findings include absence of P waves, unorganized electrical activity in their place, and irregularity of R-R interval due to irregular conduction of impulses to the ventricles. If paroxysmal AF is suspected, episodes may be documented with the use of Holter monitoring (continuous ECG recording for 24 hours or longer).

While many cases of AF have no definite cause, it may be the result of various other problems. Hence, renal function and electrolytes are routinely determined, as well as thyroid-stimulating hormone (commonly suppressed in hyperthyroidism and of relevance if amiodarone is administered for treatment) and a blood count. A chest X-ray is generally performed. In acute-onset AF associated with chest pain, cardiac troponins, or other markers of damage to the heart muscle may be ordered. Coagulation studies (INR/aPTT) are usually performed, as anticoagulant medication may be commenced. A transesophageal echocardiogram may be indicated to identify any intracardiac thrombus.

AF is linked to several cardiac causes, but may occur in otherwise normal hearts. Known associations include carbon monoxide poisoning, high blood pressure, mitral stenosis (e.g. due to rheumatic heart disease or mitral valve prolapse), mitral regurgitation, heart surgery, coronary artery disease, hypertrophic cardiomyopathy, excessive alcohol consumption ("binge drinking" or "holiday heart syndrome"), hyperthyroidism, hyperstimulation of the vagus nerve, usually by having large meals ("binge eating"), lung pathology (such as pneumonia, lung cancer, pulmonary embolism, Sarcoidosis), pericarditis, intense emotional turmoil, and congenital heart disease.

The main goals of treatment of atrial fibrillation are to prevent temporary circulatory instability and to prevent stroke. Rate and rhythm control are principally used to achieve the former, while anticoagulation may be required to decrease the risk of the latter.

AF can cause disabling and annoying symptoms. Palpitations, angina, lassitude (weariness), and decreased exercise tolerance are related to rapid heart rate and inefficient cardiac output caused by AF. There are two ways to approach these symptoms: rate control and rhythm control. Rate control treatments seek to reduce the heart rate to normal, usually 60 to 100 beats per minute. Rhythm control seeks to restore the normal heart rhythm, called normal sinus rhythm. Studies suggest that rhythm control is mainly a concern in newly diagnosed AF, while rate control is more important in the chronic phase.

AF with a persistent rapid rate can cause a form of heart failure called tachycardia induced cardiomyopathy. This can significantly increase mortality and morbidity. The early treatment of AF through either rate-control or rhythm-control can prevent this condition and thereby improve mortality and morbidity.

Rate control methods include beta blockers (e.g., metoprolol), cardiac glycosides (e.g., digoxin), and calcium channel blockers (e.g., verapamil). These medications work by slowing the generation of impulses from the atria and the conduction of those impulse from the atria to the ventricles.

In refractory cases where none of the above drugs are sufficient, a variety of other antiarrhythmic drugs, most commonly including quinidine, flecamide, propafenone, disopyramide, sotalol, or amiodarone may be used. Of these, only propafenone, sotalol, and amiodarone (which possess some beta blocking activity) control the ventricular rate; the others may maintain sinus rhythm, but may actually increase the ventricular rate. Many of these drugs are less frequently used today than in the past. All (with the possible exception of amiodarone) increase the risk of ventricular tachycardia, which can be fatal. In symptomatic patients with normal heart function, however, the small increase in risk is usually felt to be acceptable. In the presence of heart failure, the only antiarrhythmic drugs thought to be safe are amiodarone and dofetilide.

In patients with AF where rate control drugs are ineffective and it is not possible to restore sinus rhythm using cardioversion, non-pharmacological alternatives are available. For example, to control rate it is possible to destroy the bundle of cells connecting the upper and lower chambers of the heart—the atrioventricular node—which regulates heart rate, and to implant a pacemaker instead. A more complex technique involves ablating groups of cells near the pulmonary veins where atrial fibrillation is thought to originate, or creating more extensive lesions in an attempt to prevent atrial fibrillation from establishing itself.

Rhythm control methods include electrical and chemical cardioversion. Electrical cardioversion involves the restoration of normal heart rhythm through the application of a DC (direct current) electrical shock. Chemical cardioversion is performed with drugs, such as amiodarone, propafenone or flecamide. Implantable pacing devices can also be used for rate management of AF patients and can be indicated versus traditional cardioversion.

The anti-arrhythmic medications often used in either pharmacological cardioversion or in the prevention of relapse to AF alter the flux of ions in heart tissue, making them less excitable, setting the stage for spontaneous and durable cardioversion. These medications are often used in concert with electrical cardioversion.

Whichever method of cardioversion is used, approximately 50% of patients relapse within one year, although the continued daily use of oral antiarrhythmic drugs may extend this period. The key risk factor for relapse is duration of AF, although other risk factors that have been identified include the presence of structural heart disease, and increasing age.

Radiofrequency ablation (RFA) uses radiofrequency energy to destroy abnormal electrical pathways in heart tissue. It is used in recurrent AF. The energy emitting probe (electrode) is placed into the heart through a catheter. The practitioner first "maps" an area of the heart to locate the abnormal electrical activity before the responsible tissue is eliminated. Ablation is a newer technique and has shown some promise for cases unresponsive to conventional treatments. New techniques include the use of cryoablation (tissue freezing using a coolant which flows through the catheter), and microwave ablation, where tissue is ablated by the microwave energy "cooking" the adjacent tissue. The abnormal electrophysiology can also be modified in a similar way surgically, and this procedure referred to as the Cox maze procedure, is commonly performed concomitantly with cardiac surgery. More recently, minimally invasive surgical variations on the Cox Maze procedure ("minimaze" procedures) have also been developed.

The Cox maze procedure is an open-heart surgical procedure intended to eliminate atrial fibrillation. "Maze" refers to the series of incisions made in the atria (upper chambers of the heart), which are arranged in a maze-like pattern. The intention was to eliminate AF by using incisional scars to block abnormal electrical circuits (atrial macroreentry) that AF requires. This procedure required an extensive series of endocardial (from the inside of the heart) incisions through both atria, a median sternotomy (vertical incision through the breastbone) and cardiopulmonary bypass (heart-lung machine). A series of improvements were made, culminating in 1992 in the Cox maze III procedure, which is now considered to be the "gold standard" for effective surgical cure of AF. The Cox maze III is sometimes referred to as the "traditional maze", the "cut and sew maze", or simply the "maze".

Minimaze surgery is minimally invasive cardiac surgery intended to cure atrial fibrillation. Minimaze refers to "mini" versions of the original maze procedure. These procedures are less invasive than the Cox maze procedure and do not require a median sternotomy (vertical incision in the breastbone) or cardiopulmonary bypass (heart-lung machine). These procedures use microwave, radiofrequency, or acoustic energy to ablate atrial tissue near the pulmonary veins.

In confirmed AF, anticoagulant treatment is a crucial way to prevent stroke. Treatment of AF patients over age 60, who also have one or more of: previous strokes (or warning strokes), hypertension (high blood pressure), diabetes, or congestive heart failure, with warfarin (also known as COUMARIN or MAREVAN) results in a 60 to 70 percent reduction in the subsequent risk of stroke. Patients under age 65 who have any structural heart disease (i.e., valvular heart disease, ejection fraction <=35%, history of heart attack) may also benefit from warfarin.

The use of warfarin is associated with a delayed clinical effect. It typically takes three to five days to achieve a demonstrable anticoagulant effect. Hence, if an immediate anticoagulant effect is required, physicians could use heparin or other heparinoids such as enoxaparin to provide early anticoagulation. In practice, urgent anticoagulation is seldom indicated. Even in the setting of stroke complicating atrial fibrillation, clinical trial results do not support the routine use of immediate anticoagulation.

Patients under age 65 who do not have structural heart disease (i.e., with LAF) do not require warfarin, and can be treated with aspirin or clopidogrel. There is evidence that aspirin and clopidogrel are effective when used together. The new anticoagulant ximelagatran has been shown to prevent stroke with equal efficacy as warfarin.

Determining who should and should not receive anticoagulation with anti-coagulant drugs (e.g., warfarin, ximelagatran, heparin or other heparinoids) is not easy. The CHADS2 score is the best validated method of determining risk of stroke (and therefore who should be anticoagulated). The UK NICE guidelines have instead opted for an algorithm approach. The underlying problem is that if a patient has a yearly risk of stroke that is less than 2%, then the risks associated with taking warfarin outweigh the risk of getting a stroke.

EXAMPLES

The following examples are offered to illustrate, but not to limit the claimed invention.

Example 1. Biology of Stroke: Role of E112, Glipr1, Mapkapk3 Genes in Identifying Atrial Fibrillation Cause of Stroke An accurate test to identify atrial fibrillation in ischemic stroke populations would be of significant clinical utility. Using the Biomarkers of Acute Stroke Etiology (BASE) trial (NCT02014896) dataset, our goal was to utilize a database of genes appearing in literature determine if gene expression accurately differentiate patients with atrial fibrillation from those with large artery stroke.

Methods: BASE enrolled suspected stroke patients presenting to 20 hospitals within 24 hrs of symptom onset. Final gold standard diagnosis and stroke etiology were determined by an adjudication committee using all hospital data but blinded to RNA test results. Whole blood, obtained in PAXgene tubes, was frozen at −20C within 72 hrs and analyzed at a core lab (Ischemia Care, LLC, Dayton, OH) using ThermoFisher Scientific Inc. HTA micro arrays. Genes were filtered to those appearing in stroke literature resulting in 543 potential signature genes. A two-way random forest classifier was built through cross validation of the training data resulting in a 3 gene diagnostic signature with robust performance conserved across literature consisting of ELL2, GLIPR1, MAPKAPK3 genes. Results: Overall, 99 patients were enrolled with NIHSS>5, 68 (69%) with atrial fibrillation cause of stroke and 31 (31%) with large artery stroke; (48%) were male, and median (IQR) age was 74.4 (66.1, 81.7). Median (IQR) time from symptoms to blood collection was 420 (322, 472) minutes. Coexistent pathology at presentation included high blood pressure 84 (85%), hyperlipidemia 45 (45%), diabetes 31 (31%), and coronary artery disease 38 (38%). Three genes were able to differentiate atrial fibrillation from large vessel stroke; C-statistic 0.86 (0.52-1.0, 95% CI), sensitivity 0.93 (0.56-1.0, 95% CI) and specificity of 0.58 (0.35-0.81, 95% CI).

Conclusion: RNA expression of ELL2, GLIPR1, MAPKAPK3 genes differentiates atrial fibrillation stroke patients from those with large artery stroke, and may have therapeutic and outcome implications.

It is understood that the examples and embodiments described herein are for illustrative purposes only and that various modifications or changes in light thereof will be suggested to persons skilled in the art and are to be included within the spirit and purview of this application and scope of the appended claims. All publications, sequences of accession numbers, patents, and patent applications cited herein are hereby incorporated by reference in their entirety for all purposes.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. A method for diagnosing the occurrence of atrial fibrillation in ischemic stroke or a predisposition for experiencing atrial fibrillation in ischemic stroke in a human subject, the method comprising:

determining a level of mRNA expression of a plurality of atrial fibrillation in ischemic stroke-associated biomarkers in a biological sample from the subject, wherein the biomarkers are selected from the group consisting of: ELL2, GLIPR1, and MAPKAPK3;

comparing the level of expression of the atrial fibrillation in ischemic stroke-associated biomarkers to the expression level of a stably expressed endogenous reference biomarker, wherein the stably expressed endogenous reference biomarker is selected from the group consisting of: USP7, MAPRE2, CSNK1G2, SAFB2, PRKAR2A, PI4 KB, CRTC1, HADHA, MAP1LC3B, KATS, GTSE1, CDC2L1 or CDC2L2, TCF25, CHP, LRRC40, hCG 2003956 or LYPLA2 or LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHCS, C9orf23, LRRC45, NACC1, LOC100133445 or LOC115110, and PEX16;

detecting that the expression level of one or more of the atrial fibrillation in ischemic stroke-associated biomarkers is increased as compared to the expression level of the stably expressed endogenous reference biomarker;

diagnosing the occurrence of, or the predisposition for experiencing, atrial fibrillation in ischemic stroke in the subject; and administering an anticoagulant therapy to the subject.

2. The method of claim 1, wherein the expression levels of the biomarkers are concurrently or sequentially determined.

3. The method of claim 2, further comprising a step of obtaining the biological sample from the subject.

4. The method of claim 3, wherein the biological sample is blood, serum or plasma.

5. The method of claim 1, wherein the determining step is performed within 72 hours after a suspected ischemic event.

6. The method of claim 1, wherein the level of expression of the atrial fibrillation in ischemic stroke-associated biomarkers is determined by detecting hybridization of atrial fibrillation in ischemic stroke-associated gene probes to gene transcripts of the atrial fibrillation in ischemic stroke-associated biomarkers in the biological sample.

7. The method of claim 6, wherein a step of hybridization of the gene probes is performed on a nucleic acid array chip.

8. The method of claim 6, wherein a step of hybridization of the gene probes is performed in a microfluidics assay plate.

9. The method of claim 1, wherein the level of expression is determined by amplification of gene transcripts of the biomarkers.

10. The method of claim 9, wherein the amplification reaction is a polymerase chain reaction (PCR).

11. The method of claim 1 further comprising performing an electrocardiogram on the subject.

12. The method of claim 1, wherein the anticoagulant comprises at least one agent selected from the group consisting of dalteparin, danaparoid, enoxaparin, heparin, tinzaparin, and warfarin.

13. The method of claim 12, wherein the anticoagulant comprises warfarin.

* * * * *